United States Patent
Paik et al.

(10) Patent No.: US 11,833,225 B2
(45) Date of Patent: Dec. 5, 2023

(54) METHODS AND COMPOSITIONS FOR EFFICIENT GENE DELETION

(71) Applicant: CRISPR Therapeutics AG, Zug (CH)

(72) Inventors: Elizabeth Paik, Cambridge, MA (US); Mauricio Cortes, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 643 days.

(21) Appl. No.: 16/421,840

(22) Filed: May 24, 2019

(65) Prior Publication Data

US 2019/0358347 A1    Nov. 28, 2019

Related U.S. Application Data

(60) Provisional application No. 62/676,165, filed on May 24, 2018.

(51) Int. Cl.

| | |
|---|---|
| *A61K 31/5377* | (2006.01) |
| *A61K 31/7088* | (2006.01) |
| *A61K 35/28* | (2015.01) |
| *A61K 38/46* | (2006.01) |
| *C12N 9/22* | (2006.01) |
| *C12N 15/10* | (2006.01) |
| *C12N 15/11* | (2006.01) |
| *A61K 48/00* | (2006.01) |

(52) U.S. Cl.
CPC ........ *A61K 48/005* (2013.01); *A61K 31/5377* (2013.01); *A61K 31/7088* (2013.01); *A61K 35/28* (2013.01); *A61K 38/465* (2013.01); *C12N 9/22* (2013.01); *C12N 15/102* (2013.01); *C12N 15/11* (2013.01); *C12N 2310/20* (2017.05); *C12N 2800/00* (2013.01)

(58) Field of Classification Search
CPC .............. A61K 48/005; A61K 31/5377; A61K 31/7088; A61K 35/02; A61K 38/465; C12N 2310/20; C12N 9/22; C12N 15/102; C12N 15/11; C12N 2800/80
See application file for complete search history.

(56) References Cited

U.S. PATENT DOCUMENTS

| | | | |
|---|---|---|---|
| 2016/0208243 A1* | 7/2016 | Zhang | C12N 15/85 |
| 2016/0289675 A1* | 10/2016 | Ryan | C07H 21/02 |

FOREIGN PATENT DOCUMENTS

| | | |
|---|---|---|
| WO | 2014/130955 A1 | 8/2014 |
| WO | 2016/135557 A2 | 9/2016 |
| WO | 2017/147056 A1 | 8/2017 |
| WO | 2018013840 A1 | 1/2018 |
| WO | 2019/224603 A1 | 11/2019 |

OTHER PUBLICATIONS

Epstein and Schaffer, 2017. Combining Engineered Nucleases with Adeno-associated Viral Vectors for Therapeutic Gene Editing. Precision Medicine, CRISPR, and Genome Engineering, Springer, ISSN 2214-8019 (electronic), p. 33, 35-36 (Year: 2017).*
Liu and Zhao, 2018. CRISPR/Cas9 genome editing: Fueling the revolution in cancer immunotherapy Curr Res Transl Med 66, 2: 39-42 (Year: 2018).*
Jiang et al., 2013. Translating dosage compensation to trisomy 21. Nature 500, 296-300 (Year: 2013).*
Conboy et al., 2018, Making gene editing a therapeutic reality. F1000 Research 2018, 7. (Year: 2018).*
Schwank et al., 2013. Functional Repair of CFTR by CRISPR/Cas9 in Intestinal Stem Cell Organoids of Cystic Fibrosis Patients. Cell Stem Cell 13(6), 653-658 (Year: 2013).*
Nelson et al., 2016, In vivo genome editing improves muscle function in a mouse model of Duchenne muscular dystrophy. Science 51(6271), 403-407 (Year: 2016).*
Snow. Families Isolated By Rare Genetic Conditions Find New Ways To Reach Out. KQED radio. Transcript originally posted online Jun. 5, 2016 [retrieved Oct. 28, 2021] (Year: 2016).*
Ousterout et al., Multiplex CRISPR/Cas9-based genome editing for correction of dystrophin mutations that cause Duchenne muscular dystrophy, 2015. Nature Communications 6:6244, 1-13 (Year: 2015).*
Chu et al., 2015, Increasing the efficiency of homology-directed repair for CRISPR-Cas9-induced precise gene editing in mammalian cells, Nature Biotech 33(5), 543-548 and Supplemental methods and figures (Year: 2015).*
Robert et al., 2015, Pharmacological inhibition of DNA-PK stimulates Cas9-mediated genome editing. Genome Medicine 7(93), 1-11 (Year: 2015).*
Gandal et al., 2016. The road to precision psychiatry: translating genetics into disease mechanisms. Nature Neuroscience, 19(11), 1397-1407 (Year: 2016).*
Brinkman et al., Quantitative analysis shows that repair of Cas9-induced double-strand DNA breaks is slow and error-prone, bioRxiv preprint doi:https://doi.org/10.1101/142802; version posted May 26, 2017 (Year: 2017).*
Song et al., Large-scale genomic deletions mediated by CRISPR/Cas9 system. Oncotarget (2017) 8(4): 5647-5647; published Jan. 6, 2017 (Year: 2017).*
Wray et al., PARP1 is required for chromosomal translocations, Blood (2013) 121(21): 4359-4365 (Year: 2013).*
Prahallad et al., PTPN11 Is a Central Node in Intrinsic and Acquired Resistance to Targeted Cancer Drugs. Cell Reports (2015) 12: 1978-1985 and Supplemental Material (Year: 2015).*
Plasmid Data sheet 42230, http://www.addgene.org/42230/ [retrieved Apr. 28, 2022] (Year: 2022).*
K-562 cell line. https://www.atcc.org/products/ccl-243 [retrieved Apr. 28, 2022] (Year: 2022).*

(Continued)

*Primary Examiner* — Samuel C Woolwine
*Assistant Examiner* — Catherine Konopka
(74) *Attorney, Agent, or Firm* — Sheppard, Mullin, Richter & Hampton LLP

(57) ABSTRACT

Provided herein are gene-editing methods and compositions for improving the efficiency of deleting segments of DNA from cells, cells that are genetically modified using the disclosed methods and compositions, and methods of treatment using the genetically modified cells.

21 Claims, 14 Drawing Sheets

Specification includes a Sequence Listing.

(56) References Cited

OTHER PUBLICATIONS

Nelson et al., In vivo genome editing improves muscle function in a mouse model of Duchenne muscular dystrophy. 2016, Science 51(6271), 403-407 (Year: 2016).*

Park et al., 2017. DNA-PK promotes the mitochondrial, metabolic and physical decline that occurs during aging, Cell Metab. 25(5): 1135-1146 (Year: 2017).*

Han et al., Efficient in vivo deletion of a large imprinted lncRNA by CRISPR/Cas9. RNA Biology (2014), 11(7): 829-835 (Year: 2014).*

Bhargava et al., Contribution of canonical nonhomologous end joining to chromosomal rearrangements is enhanced by ATM kinase deficiency. PNAS (2017), 114(4):728-733 and Supplemental material (Year: 2017).*

International Search Report and Written Opinion from related International Application No. PCT/IB2019/000679, dated Nov. 7, 2019; 15 pgs.

Charpentier et al., "CtIP fusion to Cas9 enhances transgene integration by homology-dependent repair", Nature Communications, 2018, pp. 1-11, vol. 9.

Ye et al., "Seamless modification of wild-type induced pluripotent stem cells to the natural CCR5 32 mutation confers resistance to HIV infection", PNAS, 2014, pp. 9591-9596, vol. 111, No. 26.

Davidson, D. et al., Small molecules, inhibitors of DNA-PK, targeting DNA repair, and beyond, Frontiers In Pharmacology, 2013, vol. 4, Article 5, 7 pages.

Deltcheva, E. et al., CRISPR RNA maturation by trans-encoded small RNA and host factor RNase III, Nature, 2011, vol. 471, No. 7340, pp. 602-607.

Gribskov, M. and Burgess, R.R., Sigma factors from *E. coli, B. subtils*, phage SPOI, and phage T4 are homologous proteins, Nucleic Acids Research, 1986, vol. 14, No. 16, pp. 6745-6763.

Izzard, R.A. et al., Competitive and Noncompetitive Inhibition of the DNA-dependent Protein Kinase1, Cancer Research, 1999, vol. 59, pp. 2581-2586.

Jinek, M. et al., A programmable dual RNA-guided DNA endonuclease in adaptive bacterial immunity, Science, 2012, vol. 337, No. 6069, pp. 816-821.

Robert, F. et al., Pharmacological inhibition of DNA-PK stimulates Cas9-mediated genome editing, Genome Medicine, 2015, vol. 7, No. 93, 11 pages.

Rosenzweig, K.E. et al., Radiosensitization of human tumor cells by the phosphatidylinositol3-kinase inhibitors wortmannin and LY294002 correlates with inhibition of DNA-dependent protein kinase and prolonged G2-M delay, Clin Cancer Res., 1997, vol. 3, No. 7, pp. 1149-1156.

Ye, L. et al., Genome editing using CRISPR-Cas9 to create the HPFH genotype in HSPCs: An approach for treating sickle cell disease and ß-thalassemia, PNAS, 2016, vol. 113, No. 38, pp. 10661-10665.

* cited by examiner

SEQUENCE LISTING

<160> NUMBER OF SEQ ID NOS: 6

<210> SEQ ID NO 1
<211> LENGTH: 23
<212> TYPE: DNA
<213> ORGANISM: Homo sapiens

<400> SEQUENCE: 1
atttttctta ttcaatacct agg        23

<210> SEQ ID NO 2
<211> LENGTH: 100
<212> TYPE: RNA
<213> ORGANISM: Artificial Sequence

```
<220> FEATURE:
<223> OTHER INFORMATION: synthesized

<400> SEQUENCE: 2
auuuuucuua uucaauaccu guuuuagagc uagaaauagc aaguuaaaau aaggcuaguc    60
cguuaucaac uugaaaaagu ggcaccgagu cggugcuuuu                         100

<210> SEQ ID NO 3
<211> LENGTH: 23
<212> TYPE: DNA
<213> ORGANISM: Homo sapiens

<400> SEQUENCE: 3
ctcccccact cacagtgacc cgg                                           23

<210> SEQ ID NO 4
<211> LENGTH: 100
<212> TYPE: RNA
<213> ORGANISM: Artificial Sequence
<220> FEATURE:
<223> OTHER INFORMATION: synthesized

<400> SEQUENCE: 4 cuccccacu cacagugacc guuuuagagc uagaaauagc aaguuaaaau aaggcuaguc     60
cguuaucaac uugaaaaagu ggcaccgagu cggugcuuuu                         100

<210> SEQ ID NO 5
<211> LENGTH: 23
<212> TYPE: DNA
<213> ORGANISM: Homo sapiens

<400> SEQUENCE: 5
ctgttggttt cagagcaggt agg                                           23

<210> SEQ ID NO 6
<211> LENGTH: 100
<212> TYPE: RNA
<213> ORGANISM: Artificial Sequence
<220> FEATURE:
<223> OTHER INFORMATION: synthesized

<400> SEQUENCE: 6
cuguugguuu cagagcaggu guuuuagagc uagaaauagc aaguuaaaau aaggcuaguc    60
cguuaucaac uugaaaaagu ggcaccgagu cggugcuuuu                         100
```

METHODS AND COMPOSITIONS FOR EFFICIENT GENE DELETION

CROSS-REFERENCE TO RELATED APPLICATIONS

This application claims priority to U.S. Provisional Application Ser. No. 62/676,165, filed May 24, 2018, the disclosure of which is hereby incorporated by reference in its entirety.

SEQUENCE LISTING

This application contains a Sequence Listing that has been submitted in ASCII format via EFS-Web and is hereby incorporated by reference in its entirety. The ASCII copy, created on May 24, 2019 is named Sequence Listing.txt, and is 2 kilobytes in size.

FIELD

The present disclosure relates to methods and compositions for increasing the efficiency of targeted deletions mediated by gene editing systems.

BACKGROUND

A variety of gene editing tools are available for engineering or genetically modifying eukaryotes. The tools include the RNA-guided clustered regulatory interspaced short palindromic repeats (CRISPR) systems, zinc finger nucleases (ZFNs), and transcription activator-like effector nucleases (TALENs). The gene editing system enable efficient and precise genome modifications by inducing targeted DNA double-strand breaks (DSBs) that stimulate the cellular DNA repair mechanisms, including error-prone non-homologous end joining (NHEJ) and homology-directed repair (HDR). The efficiency of the NHEJ repair process can be problematic for gene deletion strategies that require two or more cuts in the genome to delete large segments of DNA. Strategies for improving the efficiency of NHEJ-mediated targeted gene deletions are desirable.

SUMMARY

Among the various aspects of the present disclosure are methods for increasing the efficiency of a targeted deletion of chromosomal sequence in cells by a gene editing system. The methods comprise exposing the cells to a DNA-dependent protein kinase (DNA-PK) inhibitor during generation of the targeted deletion by the gene editing system. In general, the gene editing system introduces two double-stranded breaks in the chromosomal sequence such that sequence between the two double-stranded breaks is deleted. The gene editing system can be a CRISPR-Cas system comprising two gRNAs, two zinc finger nucleases (ZFNs), or two transcription activator-like effector-based nucleases (TALENs). As disclosed herein, a variety of DNA-PK inhibitor can be used in the methods. In certain embodiments, the DNA-PK inhibitor can be Nu7441 or M3814.

Another aspect of the present disclosure encompasses methods for effecting targeted deletions of chromosomal sequence. The methods comprise (a) delivering to a population of cells (i) a CRISPR nuclease or a nucleic acid encoding a CRISPR nuclease; (ii) a first gRNA targeting a first site in chromosomal sequence and second gRNA targeting a second site in chromosomal sequence, or a nucleic acid encoding a first gRNA targeting a first site on the chromosomal sequence and a nucleic acid encoding a second gRNA targeting a second site on the chromosomal sequence; and (iii) a DNA-dependent protein kinase (DNA-PK) inhibitor, and (b) generating a deletion between the first site and the second site in chromosomal sequence, wherein the deletion in (b) occurs with greater frequency in the population of cells as compared to a population of control cells in which only (i) and (ii) are delivered.

In some embodiments, the CRISPR nuclease can be a Cas9 endonuclease or a Cpf1 endonuclease, and the CRISPR nuclease can comprise one or more nuclear localization signals (NLSs). In certain embodiments, the CRISPR nuclease *Streptococcus pyogenes* Cas9 endonuclease can be a *Staphylococcus aureus* Cas9 endonuclease. In other embodiments, each of the first and second gRNAs can be a single-molecule gRNA. As disclosed herein, a variety of DNA-PK inhibitor can be used in the methods. In certain embodiments, the DNA-PK inhibitor can be Nu7441 or M3814. The DNA-PK inhibitor can be delivered to the cells at a concentration from about 0.05 µM to about 5 µM. The DNA-PK inhibitor can be delivered to the cells at the same time, before, or after delivery of the CRISPR system. The targeted deletion can range in length from about 0.1 kilobase pair to about 100 kilobase pairs. In certain embodiments, the targeted deletion can be HPFH5 chromosomal locus or CCR5 chromosomal locus. The frequency of the targeted deletion can be increased by at least about 30% in the population of cells used in the method. The population of cells can be in vitro, ex vivo, or in vivo. In certain embodiments, the population of cell can be of human origin.

Still another aspect of the present disclosure provides genetically modified cells prepared by the methods disclosed herein. The genetically modified cells can be hematopoietic stem and progenitor cells (HSPCs), hematopoietic stem cells (HSCs), mesenchymal stem cells (MSCs), induced pluripotent stem cells (human iPSCs), or immune cells.

Yet another aspect of the present disclosure encompasses methods for treating diseases in subjects in need thereof. The methods comprise administering the genetically modified cells disclosed herein to a subject having the disease in an amount sufficient to ameliorate symptoms associated with the disease.

Additional aspects and features of the present disclosure are described below.

DETAILED DESCRIPTION

Figure 1:
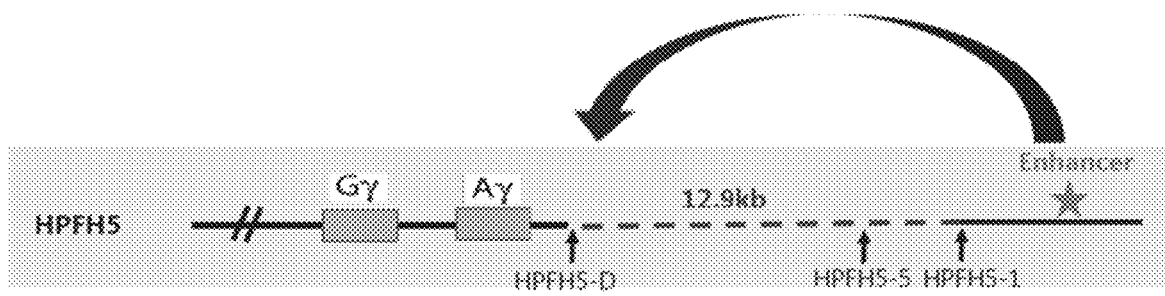
FIG. 1 is a schematic depicting the HPFH5 gene located on chromosome 11, with the location of the HPFH5-D gRNA target site, the HPFH5-5 gRNA target site, and the HPFH5-1 gRNA target site. Deletion of the 12.9 kb segment depicted by the dashed line brings the β-globin enhancer closer to γ-globin, mimicking HPFH syndrome mutations.

The present disclosure provides methods for increasing the efficiency of NHEJ-mediated targeted gene deletions in cells. The methods comprise exposing cells to an inhibitor of DNA-dependent protein kinase (DNA-PK) during generation of a targeted deletion by a gene editing system. The frequency of deletions performed in the present of the DNA-PK inhibitor is increased relative to comparable cells not exposed to the DNA-PK inhibitor. Also provided are genetically modified cells prepared by the methods disclosed herein and methods of using the methods or the genetically modified cells to treat specific diseases.

(I) Methods for Increasing Efficiency of Targeted Deletions

Provided herein are methods for increasing the efficiency of targeted deletion of chromosomal sequence in cells of interest. As detailed herein, the efficiency of targeted deletion resulting from two double-stranded breaks introduced by a gene editing system can be increased by exposing the cells to a DNA-dependent protein kinase (DNA-PK) inhibitor.

In general, double-strand breaks (DSBs) are repaired by cellular DNA repair pathways such as non-homologous end joining (NHEJ), homology-directed repair (HDR), or microhomology-mediated end joining (MMEJ). NHEJ is a robust repair mechanism that appears highly active in the majority of cell types, including non-dividing cells. NHEJ is referred to as "non-homologous" because the break ends are directly ligated without the need for a template having sequence complementarity. NHEJ is error-prone and can often result in the removal or addition of between one and several hundred nucleotides (nt) at the site of the DSB, though such modifications are typically <20 nt. The resulting insertions and deletions (indels) can disrupt coding or noncoding regions of genes. Alternatively, HDR uses a homologous donor DNA, provided endogenously or exogenously, to repair the DSB with high fidelity. HDR is active only in dividing cells, and occurs at a relatively low frequency in most cell types. The third mechanism, MMEJ uses microhomologous sequences during the repair, resulting in deletions flanking the original DNA break.

NHEJ in eukaryotes uses a number of proteins, which participate in end binding and tethering, end processing and ligation. In general, the broken ends are recognized by loading of a Ku70/Ku80 heterodimer, which then acts as a scaffold for recruitment of a DNA-dependent protein kinase (DNA-PK) catalytic subunit and a DNA ligase (XRCC4-ligase IV), which together with some accessory factors (e.g., AXX, XLF) holds the pair of DNA ends together, forming a paired end complex. The paired end complex then ligates compatible DNA ends together, thus repairing the break.

The efficiency of the NHEJ repair process often can be problematic for gene deletion strategies that require two or more DSBs in the genome to delete specific segments of chromosomal sequence. This is likely because repair could occur at one cut site before the second cut can be generated, for example. Without being bound by theory, it is thought that molecules that slow the NHEJ repair process, such as DNA-PK inhibitors, may be able to extend the period of time available for synchronization of the more than one cleavage events to create the deletion of interest. As detailed below, the frequency of targeted genome deletion is increased when gene editing is performed in the presence of a DNA-PK inhibitor.

(a) Delivering Gene Editing System

The methods described herein comprise delivering a gene editing system that can introduce two site-specific double-stranded breaks in a targeted chromosomal sequence. Suitable gene editing systems include RNA-guided CRISPR systems, zinc finger nucleases (ZFNs), and transcription activator-like effector-based nucleases (TALENs).

In some embodiments, the methods comprise delivering to cells of interest a CRISPR system comprising two guide RNAs (gRNAs), i.e., a first gRNA targeting a first site in a target nucleic acid and a second gRNA targeting a second site in the target nucleic acid, such that the sequence between the first site and the second site in the target nucleic acid can be deleted upon generation of a double-stranded break at each site by the nuclease of the CRISPR system.

In other embodiments, the methods comprise delivering to cells of interest two ZFNs (or two TALENS), wherein each ZFN (or TALEN) targets a specific site in a target nucleic acid (i.e., first and second target sites) such that the sequence between the two sites can be deleted upon generation of a double-stranded break at each site by the ZFNs (or TALENs).

The distance between the first and second sites in the target nucleic acid can and will vary. In general, the distance between the two sites can range from about 0.1 kilobase pair (kb) to about 100 kb. In various embodiments, the distance between the two targeted sites can range from about 0.1 kb to about 1 kb, from about 1 kb to about 3 kb, from about 3 kb to about 10 kb, from about 10 kb to about 30 kb, or from about 30 kb to about 100 kb.

(i) CRISPR Systems

The RNA-guided clustered regularly interspaced short palindromic repeats (CRISPR) system is a naturally-occurring defense mechanism in prokaryotes and archaea that has been repurposed as a RNA-guided DNA-targeting platform used for gene editing. A CRISPR system comprises a noncoding guide RNA (gRNA) to target the DNA and a nuclease (e.g., Cas9, Cpf1, etc.) that cleaves the DNA.

The gRNA drives sequence recognition and specificity of the CRISPR-Cas9 complex through Watson-Crick base pairing typically with a ~20 nucleotide (nt) sequence in the target DNA that is adjacent to a specific short DNA motif referred to as a protospacer adjacent motif (PAM). The gRNA forms an RNA-duplex structure that is bound by the CRISPR-Cas9 nuclease to form the catalytically active CRISPE-Cas9 complex, which can then cleave the target DNA. Once the CRISPR-Cas9 complex is bound to DNA at a target site, two independent nuclease domains within the Cas9 nuclease each cleave one of the DNA strands three bases upstream of the PAM site, leaving a double-strand break (DSB) where both strands of the DNA terminate in a base pair (a blunt end).

In some embodiments, the CRISPR-Cas9 endonuclease may be a Type II protein from *Streptococcus pyogenes* (SpCas9; PAM=NRG) or *Staphylococcus aureus* (SaCas9; PAM=NNGRRT or NNGRRN), although other Cas9 homologs, orthologs, and/or variants (e.g., evolved versions of Cas9) may be used, as provided herein. Additional non-limiting examples of CRISPR nucleases that may be used herein include Cpf1 (Type V; PAM=TTN); SpCas9 D1135E variant (PAM=NAG or NGA); SpCas9 VRER variant (PAM=NGCG); SpCas9 EQR variant (PAM=NGAG); SpCas9 VQR variant (PAM=NGAN or NGNG); *Neisseria meningitidis* (NmCas9; PAM=NNNNGATT); *Streptococcus thermophilus* (StCas9; PAM=NNAGAAW); and *Treponema denticola* (TdCas9; PAM=NAAAAC), wherein N is any nucleotide, R is either A or G, and W is either A or T.

The CRISPR nuclease can be fused to one or more nuclear localization signal (NLS) at the N-terminal end, the C-terminal end, or both. NLSs are well known in the art. For example, the NLS can be the SV40 Large T-antigen NLS, nucleoplasmin NLS, c-Myc NLS, or derivatives thereof.

A gRNA comprises at least a spacer sequence that hybridizes to a target sequence (at a target site), and a CRISPR repeat sequence. In Type II systems (e.g., *Streptococcus pyogenes* systems), the gRNA also comprises a tracrRNA (trans-activating RNA) sequence. In Type II systems, the CRISPR repeat sequence and tracrRNA sequence hybridize to each other to form a duplex. A type II system gRNA can be a single molecule (i.e., single-molecule gRNA or sgRNA) or can comprise two separate molecules (e.g., crRNA and tracrRNA). In Type V systems, a crRNA (CRISPR RNA) sequence forms a duplex. In both systems, the duplex binds a RNA-guided nuclease (e.g., Cas9) such that the gRNA and the RNA-guided nuclease form a complex. The gRNA, thus, directs the activity of the RNA-guided nuclease.

The spacer sequence of the gRNA is a sequence (e.g., a 20 nucleotide) that defines the target sequence of a target nucleic acid (e.g., genomic sequence). The "target sequence" is adjacent to a PAM sequence and is a sequence modified by an RNA-guided nuclease (e.g., Cas9). The "target nucleic acid" is a double-stranded molecule: one strand comprises the target sequence and is referred to as the "PAM strand," and the other complementary strand is referred to as the "non-PAM strand." One of skill in the art recognizes that the gRNA spacer sequence hybridizes to the reverse complement of the target sequence, which is located in the non-PAM strand of the target nucleic acid. The spacer of a gRNA interacts with a target nucleic acid in a sequence-specific manner via hybridization (i.e., base pairing). The nucleotide sequence of the spacer thus varies depending on the target sequence of the target nucleic acid.

In some embodiments, the spacer sequence of the gRNA may be 15 to 30 nucleotides long, or 18 to 22 nucleotides long. In some embodiments, the spacer sequence is 15, 16, 17, 18, 19, 29, 21, 22, 23, 24, 25, 26, 27, 28, 29, or 30 nucleotides. In some embodiments, a spacer sequence is 20 nucleotides long. (See, e.g., Jinek et al., Science, 337, 816-821 (2012) and Deltcheva et al., Nature, 471, 602-607 (2011)). In general, the spacer sequence has at least about 90%, at least about 95%, or at least about 99% sequence identity to the target sequence in the target nucleic acid. In certain embodiments, the spacer sequence has 100% sequence identity to the target sequence.

In some embodiments, a gRNA in a Type II system can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The guide linker links the minimum CRISPR repeat and the minimum tracrRNA sequence to form a hairpin structure. The optional tracrRNA extension may comprise one or more hairpins. A gRNA in a Type V system can comprise, in the 5' to 3' direction, a minimum CRISPR repeat sequence and a spacer sequence.

The gRNA, in some embodiments, can comprise one or more uracil at the 3' end of the gRNA sequence. For example, the gRNA may comprise one (U), two (UU), three (UUU), four (UUUU) or more uracils at the 3' end of the gRNA sequence. In some embodiments the gRNA comprises 5, 6, 7, or 8 uracils at the 3' end of the gRNA sequence. In some embodiments the gRNA comprises 1 to 8, 2 to 8, 3 to 8, or 4 to 8 uracils at the 3' end of the gRNA sequence.

The gRNA can be unmodified or modified. For example, modified gRNAs may comprise one or more 2'-O-methyl phosphorothioate nucleotides. For example, the gRNA may comprise 2'-O-methyl-phosphorothioate residues at the 5' end/or the 3' end. In some embodiments, the gRNA comprises three 2'-O-methyl-phosphorothioate residues at the 5' end and 2'-O-methyl-phosphorothioate residues at the 3' end.

By way of illustration, gRNAs used in the CRISPR system can be readily synthesized by chemical means, as described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

(ii) ZFNs and TALENs

ZFNs are engineered proteins comprising zinc finger (ZF) DNA-binding domains fused to a DNA-cleavage domain. The ZF domains can be engineered to target specific DNA sequences, and the cleavage domain is generally derived from a Type IIS restriction enzyme, e.g., FokI. A ZFN is a heterodimer in which each subunit contains a DNA binding domain and a FokI cleavage half-domain. The ZFNs binds specific sites at opposite DNA strands, the FokI half-domains dimerize, thereby generating a double-stranded break.

TALENs are engineered proteins comprising DNA binding domains derived from transcription activator-like effectors (TALEs), which are transcription factors from the plant pathogen *Xanthomonas*. TALEs can be engineered to target specific DNA sequences and are linked to a DNA cleavage domain, e.g., FokI. As with ZFNs, TALENs are heterodimers comprising FokI cleavage half domains.

(iii) Delivery Means

The gene editing systems can be introduced into the cells as purified isolated systems (e.g., RNP complexes or proteins, depending upon the type of system) or as nucleic acids encoding the system. The nucleic acid can be DNA or RNA. In embodiments in which the encoding nucleic acid is mRNA, the mRNA may be 5' capped and/or 3' polyadenylated. In embodiments in which the encoding nucleic acid is DNA, the DNA can be linear or circular. In embodiments in which the gene editing system is a CRISPR system, the DNA encoding the CRISPR nuclease generally is codon optimized for expression in the cells of interest. The nucleic acid can be part of a plasmid or viral vector, wherein the encoding nucleic acid can be operably linked to a suitable promoter. Those skilled in the art are familiar with appropriate vectors, promoters, other control elements, and means of introducing the vector into the cell of interest.

In embodiments in which the gene editing system is a CRISPR system, the CRISPR system can be delivered to the cell as a gRNA-protein (RNP) complex. Alternatively, RNA or DNA encoding the CRISPR protein can be delivered, and gRNAs can be delivered as RNA or coding DNA. In one embodiment, DNA encoding the CRISPR nuclease and DNA encoding gRNAs can be delivered via a single vector or via different vectors. In some embodiments, the gRNAs and CRISPR nuclease can be delivered in a 1:1 molar ratio; however, this ratio may vary.

The gene editing system can be delivered to the cells by a variety of methods. Suitable methods include electroporation (e.g., nucleofection) and other transfection means.

(iv) Target Nucleic Acids

Target nucleic acids of the present disclosure can comprise DNA, RNA, genomic nucleic acids, or episomal nucleic acids. In specific embodiments, the target nucleic acid is a genomic nucleic acid, such as a chromosomal nucleic acid (or chromosomal sequence). Many chromosomal abnormalities are known, including structural abnormalities, which may be corrected using the gene editing technology as provided herein. Chromosomal abnormalities may be associated with any of the 46 (23 pairs) of human chromosomes (including autosomes and sex chromosomes). Examples of structural abnormalities include deletions, duplications, translocations, and inversions.

In some embodiments, a specific exon of a gene may be targeted for deletion. Such deletions may be single-exon deletions or multi-exon (more than one exon) deletions. Deletions may also be targeted in enhancer, promoter, intron, an untranslated region (UTR), and/or in other regulatory elements.

In certain situations, a targeted deletion can be used to silence or knockout gene expression. Non-limiting examples of genes to knockout include C-C motif chemokine receptor (CCR5) to counter HIV infection, T cell specific genes (e.g., programmed cell death protein 1 (PD-1), T-cell receptor (TCR), etc.) to generate T cells with increased anti-tumor activity, and the XIST gene in Down's syndrome.

In other embodiments, targeted deletions can be used to reactivate gene expression. For example, deletion in the δ-globin locus can bring an enhancer closer to the fetal γ-globin gene and activate expression of the fetal gene. Similarly, deletion of the erythroid-specific enhancer region of the BCL11A gene can reactivate fetal γ-globin expression.

In still other embodiments, targeted deletions can be used to restore the correct reading frame in mutant genes such as the Duchenne muscular dystrophy (DMD) gene. Similarly, targeted deletions can be used to eliminate repeats present in trinucleotide repeat disorders, e.g., Huntington's disease (HTT gene), spinocerebellar ataxics (e.g., ATXN1,2,3,7, CACNA1A, TBP, SCA8, PPP2R2B genes), fragile X syndrome (FMR1 gene), myotonic dystrophy (DMPK gene), Friedreich's ataxia (FXN gene), juvenile myoclonic epilepsy, etc.

(b) Delivering DNA-PK Inhibitor

The methods disclosed herein also comprise exposing or delivering to the cells of interest an inhibitor of DNA-dependent protein kinase (DNA-PK). DNA-PK participates in repair of DSBs in DNA by activating the NHEJ pathway. DNA-PK is a trimeric protein complex that includes a serine/threonine protein kinase, a DNA-PK catalytic subunit (DNA-PKcs), and a DNA targeting heterodimer Ku70 and Ku80. DNA-PK is activated upon association with DNA.

A DNA-PK inhibitor is any agent (e.g., compound) that can inhibit (reduce) DNA-PK activity by at least 10%. In some embodiments, a DNA-PK inhibitor inhibits DNA-PK activity by at least 20%, at least 30%, at least 40%, at least 50%, at least 60%, at least 70%, at least 80%, or at least 90%. In some embodiments, a DNA-PK inhibitor inhibits DNA-PK activity by 10% to 90%, 20% to 90%, 30% to 90%, 40% to 90%, or 50% to 90%. Methods for assaying DNA-PK activity are known. For example, a conventional kinase assay may be used, whereby radio-labeled phosphate incorporation into a peptide substrate is assayed. In some embodiments, the DNA-PK inhibitor inhibits DNA-PK activity for a time sufficient to enable a targeting endonuclease (e.g., an RNA-guided nuclease) to catalyze two or more DSBs in a target nucleic acid, before the DBSs are repaired, e.g., by the NHEJ process.

A variety of DNA-PK inhibitors are suitable for use on the methods disclosed herein. The viridins, such as wortmannin and the quercitins, are natural product classes, the members of which inhibit both DNA-PK and closely related phosphatidylinositol 3-kinases (Izzard et al., Cancer. Res., 1999, 59: 2581-2586). Specific, non-limiting examples of DNA-PK inhibitors that may be used as provided herein include: Nu7441 (8-(4-dibenzothienyl)-2-(4-morpholinyl)-4H-1-benzopyran-4-one), M3814 (S)-(2-chloro-4-fluoro-5-(7-morpholinoquinazolin-4-yl)phenyl)(6-methoxypyridazin-3-yl)methanol, PI 103 hydrochloride (3-[4-(4-morpholinylpyrido[3',2':4,5]furo[3,2-d]pyrimidin-2-yl] phenol hydrochloride); DMNB (4,5-dimethoxy-2-nitrobenzaldehyde); NU 7026 (2-(4-morpholinyl)-4H-naphthol[1,2-b]pyran-4-one), compound 401 (2-(4-morpholinyl)-4H-pyrimido[2,1-a]isoquinolin-4-one), ETP 45658 (3-[1-methyl-4-(4-morpholinyl)-1H-pyrazolo[3,4-d] pyrimidin-6-ylphenol), KU 0060648 (4-ethyl-N-[4-[2-(4-morpholinyl)-4-oxo-4H-1-benzopyran-8-yl]-1-dibenzothienyl]-1-piperazineacetamide), LTURM 34 (8-(4-dibenzothienyll)-2-(4-morpholinyl)-4H-1,3-benzoxazin-4-one), 1-(2-hydroxy-4-morpholin-4-yl-phenyl)-ethanone; PIK-75 HCl (2-methyl-5-nitro-2-[(6-bromoimidazo[1,2-a] pyridin-3-yl)methylene]-1-methylhydrazide-benzenesulfonic acid, monohydrochloride); CC-115 (1-ethyl-7-(2-methyl-6-(1h-1,2,4-triazol-3-yl)pyridin-3-yl)-3,4-dihydropyrazino(2,3-b)pyrazin-2(1h)-one), SU1152 (Ismail H I, et la. Oncogene 23: 873-882, 2004); rutin and LY294002 (Rosenzweig et al., Clin. Cancer Res. 1997, 3:1149-1156); OK1035, IC86621, IC87102, IC87361, IC486241, SU11752, NK314, and vanillin (Davidson et al., Frontiers Pharmacol., 2013, 4, Article 5, 7 pp); and derivatives thereof. In some embodiments, the DNA-PK inhibitor is Nu7441. In other embodiments, the DNA-PK inhibitor is M3814.

The concentration of the DNA-PK inhibitor can and will vary depending upon the identity of the inhibitor. In general, the concentration of the DNA-PK inhibitor can range from about 0.0001 µM to about 10 µM. In certain embodiments, the concentration of the DNA-PK inhibitor can range from about 0.0001 µM to about 0.001 µM, from about 0.001 µM to about 0.01 µM, from about 0.01 µM to about 0.1 µM, from about 0.1 µM to 1 µM, or from about 1 µM to about 10 µM.

In embodiments in which the cells are isolated cells, the DNA-PK inhibitor can be added to the medium used to incubate the cells during the gene editing process. In embodiments in which the cells are within a subject, the DNA-PK inhibitor can be administered orally or parenterally (e.g., intravenous, intramuscular, or subcutaneous) to the subject.

In some embodiments, the DNA-PK inhibitor can be delivered to the cells at about the same time (i.e., simultaneously) as the gene editing system. In other embodiments, the DNA-PK inhibitor can be delivered to the cells prior to delivery of the gene editing system. In still other embodiments, the DNA-PK inhibitor can be delivered to the cells after to delivery of the gene editing system.

(c) Generating Targeted Deletions

The methods disclosed herein further comprise incubating the cells under conditions that allow the gene editing system to introduce DSBs at the first and second target sites in the target nucleic acid (e.g., chromosomal sequence), wherein the DSBs can be repaired by NHEJ-mediated ligation of the distal chromosomal cut ends such that the sequence between the first and second sites is deleted. The presence of the DNA-PK inhibitor appears to slow repair of the double-stranded breaks by NHEJ such that the efficiency of deletion is increased relative to cells comprising the gene editing system but not exposed to the DNA-PK inhibitor. In general, the efficiency of deletion is measured by the frequency of deletion in a population of cells.

The size of the deletion can and will vary. In general, the size of the deletion can range from about 0.1 kb to about 100 kb. In various embodiments, the size of the deletion can range from about 0.1 kb to about 1 kb, from about 1 kb to about 3 kb, from about 3 kb to about 10 kb, from about 10 kb to about 30 kb, or from about 30 kb to about 100 kb.

As detailed in the examples below, the efficiency and/or frequency of deletions preformed in the presence of a DNA-PK inhibitor is increased relative to comparable cells not exposed to the DNA-PK inhibitor. In various embodiments, the deletion frequency may be increased from about 10% to about 30%, from about 30% to about 60%, from about 60% to about 100%, from about 1-fold to about 2-fold, from about 2-fold to about 4-fold, from about 4-fold to about 6-fold, from about 6-fold to about 10-fold, from about 10-fold to about 20-fold, from about 20-fold to about 50-fold, or more than about 50-fold relative to comparable cells not exposed to the DNA-PK inhibitor.

In some embodiments, the targeted deletion can be on one of a pair of chromosomes. Such deletions are termed heterozygous. In other embodiments, both chromosomes can comprise the targeted deletion, and the deletion is termed homozygous.

(d) Cells

A variety of cell can be used in the methods disclosed herein. In general, the cells are eukaryotic cells. In some embodiments, the cells are mammalian cells. In specific embodiments, the cells are human cells.

The cells can be in vitro (e.g., cell line cells, cultured cells, primary cells), can be ex vivo cells isolated from an organism, or can be in vivo cells within an organism.

In some embodiments, the cells may be stem cells (e.g., embryonic, fetal, amniotic, or adult stem cells). In certain embodiments, the stem cells may be adult stem cells isolated from bone marrow, adipose tissue, or blood. In embodiments, the stem cells may be isolated from umbilical cord. In still other embodiments, the cells may be induced pluripotent stem cells (e.g., human iPSCs).

In particular embodiments, the cells may be hematopoietic stem and progenitor cells (HSPCs) or hematopoietic stem cells (HSCs). HSPCs give rise to all blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells). Blood cells are produced by the proliferation and differentiation of a very small population of pluripotent HSCs that also have the ability to replenish themselves by self-renewal. During differentiation, the progeny of HSCs progress through various intermediate maturational stages, generating multi-potential and lineage-committed progenitor cells prior to reaching maturity. Bone marrow (BM) is the major site of hematopoiesis in humans and, under normal conditions, only small numbers of HSPCs can be found in the peripheral blood (PB). Treatment with cytokines (in particular granulocyte colony-stimulating factor; G-CSF), some myelosuppressive drugs used in cancer treatment, and compounds that disrupt the interaction between hematopoietic and BM stromal cells can rapidly mobilize large numbers of stem and progenitors into the circulation. The cell surface glycoprotein CD34 is routinely used to identify and isolate HSPCs.

In other embodiments, the cells may be mesenchymal stem cells (e.g., multipotent stromal cells that can differentiate into a variety of cell types). Mesenchymal stem cells (MSCs) are adult stem cells found in the bone marrow, or isolated from other tissues such as cord blood, peripheral blood, fallopian tube, and fetal liver and lung. As multipotent stem cells, MSCs differentiate into multiple cell types including adipocytes, chondrocytes, osteocytes, and cardiomyocytes. Mesenchymal stem cells are a distinct entity to the mesenchyme, embryonic connective tissue, which is derived from the mesoderm and differentiates to form hematopoietic stem cells (HPCs).

In still other embodiments, the cells may be immune cells such as T cells, B cells, natural killer (NK) cells, NKT cells, mast cells, eosinophils, basophils, macrophages, neutrophils, or dendritic cells.

(II) Genetically Modified Cells

The present disclosure also provides genetically-modified cells, for example, those produced by the methods as described above in section (I). A genetically modified cell is a cell that comprises at least one genome modification (e.g., insertion, deletion, and/or mutation). In general, the genetically modified cells provided herein comprise at least one deletion of chromosomal sequence as introduced by the methods provided herein. In some aspects, the genetically modified cells provided herein further comprise the gene editing system and the DNA-PK inhibitor. In certain embodiments, the genetically modified cell can comprise additional genome modifications (e.g., insertions, deletions, and/or mutations) as introduced by the gene editing systems describe herein.

The genetically modified cells can be any of the cells described above in section (I)(d), derivatives thereof, or descendants thereof (e.g., differentiated cells derived from genetically modified stem cells or progenitor cells).

In some embodiments, the genetically modified cells can be generated in vitro from cells isolated from a subject, the genetically modified cells can be expanded and/or differentiated, and then the genetically modified cells or derivatives thereof can be transplanted back into the subject. In other embodiments, the genetically modified cells can be generated in vivo, i.e., within a subject.

(III) Methods for Treating Diseases

Also provided herein are methods for treating and/or preventing diseases. In some embodiments, the methods can comprise administering genetically modified cells as described herein to a subject having the disease in an amount sufficient to ameliorate symptoms associated with the disease In other embodiments, the methods can comprise generating genetically modified cells in situ in a subject having the disease, such that symptoms associated with the disease are ameliorated.

In some embodiments, the methods and compositions provided herein can be used to treat hemoglobinopathies. Examples of hemoglobinopathies include sickle cell disease and β-thalassemia, which are due to mutant forms of β-globin or reduced levels of β-globin. Targeted deletions in the β-globin gene locus can lead to reactivation of fetal γ-globin. Such deletions mimic naturally occurring mutations that occur in hereditary persistence of fetal hemoglobin (HPFH) disorders in which continued expression of fetal hemoglobin during adulthood mitigate effects of sickle cell disease or β-thalassemia. In alternate embodiments, deletion of an erythroid-specific enhancer region in the BCL11A gene can reactivate fetal γ-globin expression. Genetically modified cells comprising one of these deletions can be generated using the methods disclosed herein, and then introduced back into patient.

In other embodiments, the methods and compositions provided herein can be used to prevent HIV infection by inactivating the C-C motif chemokine receptor (CCR5), the major coreceptor used by HIV-1 and HIV-2. Targeted deletion of all or part of the CCR5 can result in its inactivation In additional embodiments, the methods and compositions provided herein can be used to treat cancers. For example, knock out of specific T cell genes (e.g., programmed cell death protein 1 (PD1), T-cell receptor (TCR), etc.) by a targeted gene deletion can be used to generated tumor-specific T cells with improved efficacy profiles.

In still other embodiments, the methods and compositions provided herein can be used to treat Down's syndrome by inactivating the XIST gene by a targeted deletion.

In other embodiments, targeted deletions can be used to restore the correct reading frame in mutant genes. Diseases that can be treated with such an approach include Duchenne muscular dystrophy, Huntington's disease, spinocerebellar ataxias, fragile X syndrome, myotonic dystrophy, Friedreich's ataxia and juvenile myoclonic epilepsy.

Definitions

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some (e.g., 70%) of the bases are complementary. The bases that are not complementary are "mismatched."

Complementarity may also be complete (i.e., 100%), if all the bases in the duplex region are complementary.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The terms "nuclease" and "endonuclease" are used interchangeably herein, and refer to an enzyme that cleaves both strands of a double-stranded nucleic acid sequence.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine), nucleotide isomers, or nucleotide analogs. A nucleotide analog refers to a nucleotide having a modified purine or pyrimidine base or a modified ribose moiety. A nucleotide analog may be a naturally occurring nucleotide (e.g., inosine, pseudouridine, etc.) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The term "sequence identity" as used herein, indicates a quantitative measure of the degree of identity between two sequences of substantially equal length. The percent identity of two sequences, whether nucleic acid or amino acid sequences, is the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website.

The term "targeted deletion" refers to a deletion of at least one nucleotide base pair at a specific site in a target nucleic acid by a gene editing system that is engineered to target the specific site.

The terms "target sequence," "target site," and "site" are used interchangeably to refer to the specific sequence in a target nucleic acid to which the gene editing system is targeted.

The terms "treating" or "treatment," as used herein, refer to alleviating, ameliorating, or inhibiting the symptoms of a disease or disorder; reversing, inhibiting, or slowing the progression of a disease or disorder; and/or preventing or delaying the onset of a disease or disorder.

Where a range of values is provided, each value between the upper and lower ends of the range are specifically contemplated and described herein.

EXAMPLES

The following examples illustrate various non-limiting embodiments of the present disclosure.

Example 1. Deletions in HPFH5 Using Dual gRNAs

The syndrome of hereditary persistence of fetal hemoglobin (HPFH) comprises a large number of genetic mutations primarily of the β-globin gene cluster, resulting in elevated fetal hemoglobin (HbF) levels persisting into adulthood. To mimic a HPFH syndrome deletion mutation, a 12.9 kb segment in the β-globin locus was targeted for deletion. FIG. 1 diagrams the hereditary persistence of fetal hemoglobin 5 (HPFH5) gene, which is located on chromosome 11, with the location of a 5' gRNA target site (HPFH5-D gRNA) and two 3' gRNA target sites (HPFH5-5 gRNA and HPFH5-1 gRNA). Deletion of the segment depicted by the dashed line brings the β-globin enhancer closer to γ-globin, which may lead to increased expression of γ-globin. The target site sequences, with the PAM in bold, and the gRNA sequences, with the spacer underlined, are presented below in Table 1.

TABLE 1

| Target and RNA sequences | | |
|---|---|---|
| | 5'-3' | SEQ ID NO: |
| HPFH5-1 target sequence | ATTTTTCTTATTCAATACCTAGG | 1 |
| HPFH5-1 gRNA | <u>AUUUUUCUUAUUCAAUACCUGUU</u>UUAGAGCUAGAAAUAGCAAGUUAAAAUAAGGCUAGUCCGUUAUCAACUUGAAAAAGUGGCACCGAGUCGGUGCUUUU | 2 |

TABLE 1-continued

Target and RNA sequences

| | 5'-3' | SEQ ID NO: |
|---|---|---|
| HPFH5-5 target sequence | CTCCCCCACTCACAGTGACCCGG | 3 |
| HPFH5-5 gRNA | CUCCCCCACUCACAGUGACCGUU UUAGAGCUAGAAAUAGCAAGUUA AAAUAAGGCUAGUCCGUUAUCAA CUUGAAAAAGUGGCACCGAGUCG GUGCUUUU | 4 |
| HPFH5-D target sequence | CTGTTGGTTTCAGAGCAGGTAGG | 5 |
| HPFH5-D gRNA | CUGUUGGUUUCAGAGCAGGUGUU UUAGAGCUAGAAAUAGCAAGUUA AAAUAAGGCUAGUCCGUUAUCAA CUUGAAAAAGUGGCACCGAGUCG GUGCUUUU | 6 |

Mobilized human peripheral blood (mPB) CD34+ cells from three independent human donors were cultured in serum free CellGro® media including 100 ng/ml recombinant human stem cell factor (SCF), 100 ng/ml recombinant human Flt 3-Ligand (FLT3L), and 100 ng/ml Thrombopoietin (TPO). 100,000 cells per condition were electroporated using Lonza Amaxa 4D electroporator without any CRISPR/Cas9 editing components as a negative control (mock electroporation sample), with HPFH5-1+HPFH5-D sgRNAs and Cas9 protein (1+D), or with HPFH5-5+HPFH5-D sgRNAs and Cas9 protein (5+D). The recombinant S. pyogenes Cas9 protein was flanked by two SV40 nuclear localization sequences (NLSs). These experiments were performed using a ribonucleoprotein (RNP) 1:1 weight ratio of gRNA to Cas9.

Figure 2:
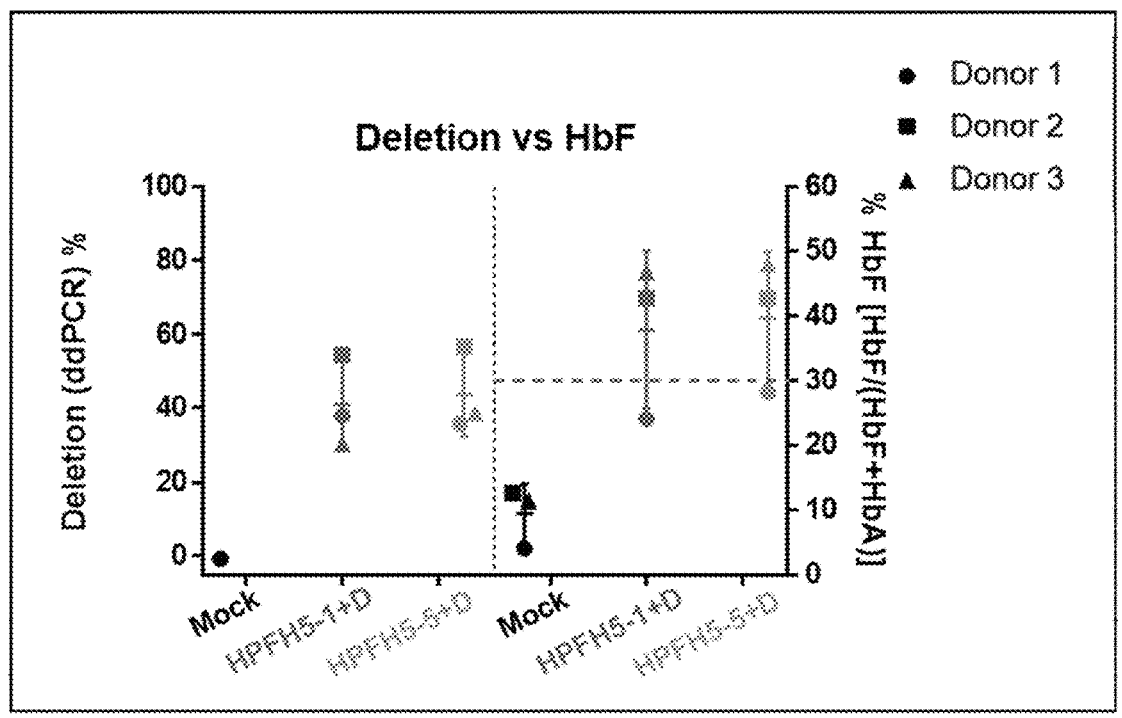
FIG. 2 is a graph showing the percentage of HPFH5 deletions (left axis) and percentage of fetal hemoglobin (HbF) (right axis) in CD34+ human hematopoietic stem and progenitor cells (hHSPCs) from three independent healthy donors, edited with Cas9 and the indicated gRNA pairs: mock; HPFH5-1 gRNA+HPFH5-D gRNA; or HPFH5-5 gRNA+HPFH5-D gRNA. The data demonstrates that baseline deletions that mimic HPFH5 induce an increase in the relative amount of HbF.

The deletion frequency was determined by droplet digital PCR (ddPCR) two days after electroporation for each cell population (i.e., mock, 1+D, and 5+D). CRISPR-Cas9 editing with either set of dual gRNAs resulted in about 40% deletion efficiency (FIG. 2, left axis).

The cells were switched to an erythroid differentiation medium (IMDM+Glutamax supplemented with 5% human serum, 10 µg/ml insulin, 20 ng/ml SCF, 5 ng/ml IL-3, 3 U/ml EPO, 1 µM dexamethasone, 1 µM β-estradiol, 330 µg/ml holo-transferrin and 2 U/ml heparin). The gene-edited mPB CD34+ cells that differentiated into erythrocytes were further tested on Day 18 for expression of HbF tetrameric protein via FACS and ion-exchange HPLC (IEX-HPLC). Each of the gene-edited cells showed approximately a 30% increase in HbF protein expression (HbF/(HbF+HbA)) over the negative (mock) control (FIG. 2, right axis). Percent HbF was calculated by normalizing HbF levels to adult hemoglobin (HbA) levels.

Example 2. Single Versus Dual gRNA and Cas9 Titrations

Single HPFH5-1, HPFH5-5 and HPFH5-D gRNAs, as well as Cas9 protein, were titrated in CD34+ hHSPCs to determine the effects on deletion efficiency. Single gRNA editing efficiency increased in a dose-dependent manner, as shown in Table 2.

TABLE 2

Single gRNA Editing Percentage 48 Hours Post Electroporation
% Single Guide Editing: 48 hour post-electroporation

| gRNA amount (µg) | Cas9 amount (µg) | HPFH5-1 | HPFH5-5 | HPFH5-D |
|---|---|---|---|---|
| 1 | 1 | 35.6 | 40.5 | 20.8 |
| 2 | 2 | 62.9 | 56.5 | 61.4 |
| 3 | 3 | 72.1 | 60.3 | 70.9 |
| 4 | 4 | 75.7 | 66.3 | 80.4 |

Figure 3:
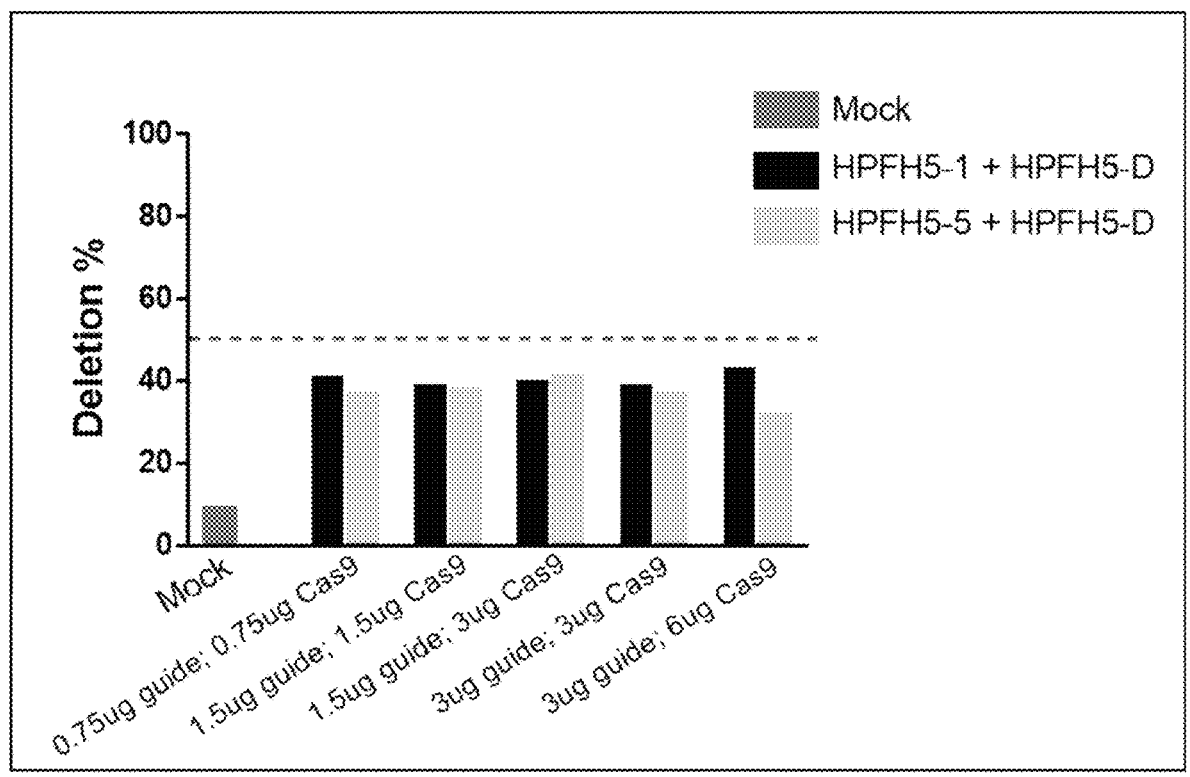
FIG. 3 is a graph showing the percentage of HPFH5 deletions in CD34+ hHSPCs edited with increasing doses of Cas9 and the indicated gRNA pairs at 72 hours post electroporation. The deletion percentage was relatively consistent across all Cas9 and gRNA concentrations tested.

Dual gRNAs (HPFH5-1 and HPFH-D, or HPFH5-5 and HPFH-D), as well as Cas9 protein, were also titrated in CD34+ hHSPCs. Surprisingly, the deletion efficiency, as measured by ddPCR, in cells edited with CRISPR-Cas9 using dual gRNAs did not change within increasing concentrations of gRNA or Cas9 protein. CRISPR-Cas9 editing with HPFH5-1 and HPFH5-D or with HPFH5-5 and HPFH5-D resulted in about 40% deletion efficiency (FIG. 3).

Example 3. HPFH5 Deletions Using Dual gRNAs and DNA-PK Inhibitor Nu7441

Mobilized human peripheral blood (mPB) CD34+ cells from a human donor were cultured in serum free CellGro® media including 100 ng/ml recombinant human stem cell factor (SCF), 100 ng/ml recombinant human Flt 3-Ligand (FLT3L), and 100 ng/ml Thrombopoietin (TPO). 100,000 cells per condition were electroporated using Lonza Amaxa 4D electroporator without any CRISPR/Cas9 editing components as a negative control (mock electroporation sample), with HPFH5-1+HPFH5-D sgRNAs and Cas9 protein (1D), or with HPFH5-5+HPFH5-D sgRNAs and Cas9 protein (5D). The recombinant S. pyogenes Cas9 protein was flanked by two SV40 nuclear localization sequences (NLSs). These experiments were performed using a ribonucleoprotein (RNP) 1:1 weight ratio of gRNA to Cas9.

To test whether inhibiting NHEJ repair increases deletion efficiency in CD34+ hHSPCs edited with CRISPR-Cas9 and the dual gRNAs, Nu7441 was delivered to the cells at various concentrations right after electroporation. Cells were seeded at 500K/mL density in the serum free CellGro® media including 100 ng/ml recombinant human stem cell factor (SCF), 100 ng/ml recombinant human Flt 3-Ligand (FLT3L), 100 ng/ml thrombopoietin (TPO), with various concentrations of Nu7441 (e.g., 0.3125 µM, 0.625 µM, 1.25 µM, 2.5 µM, or 5 µM).

Figure 4:
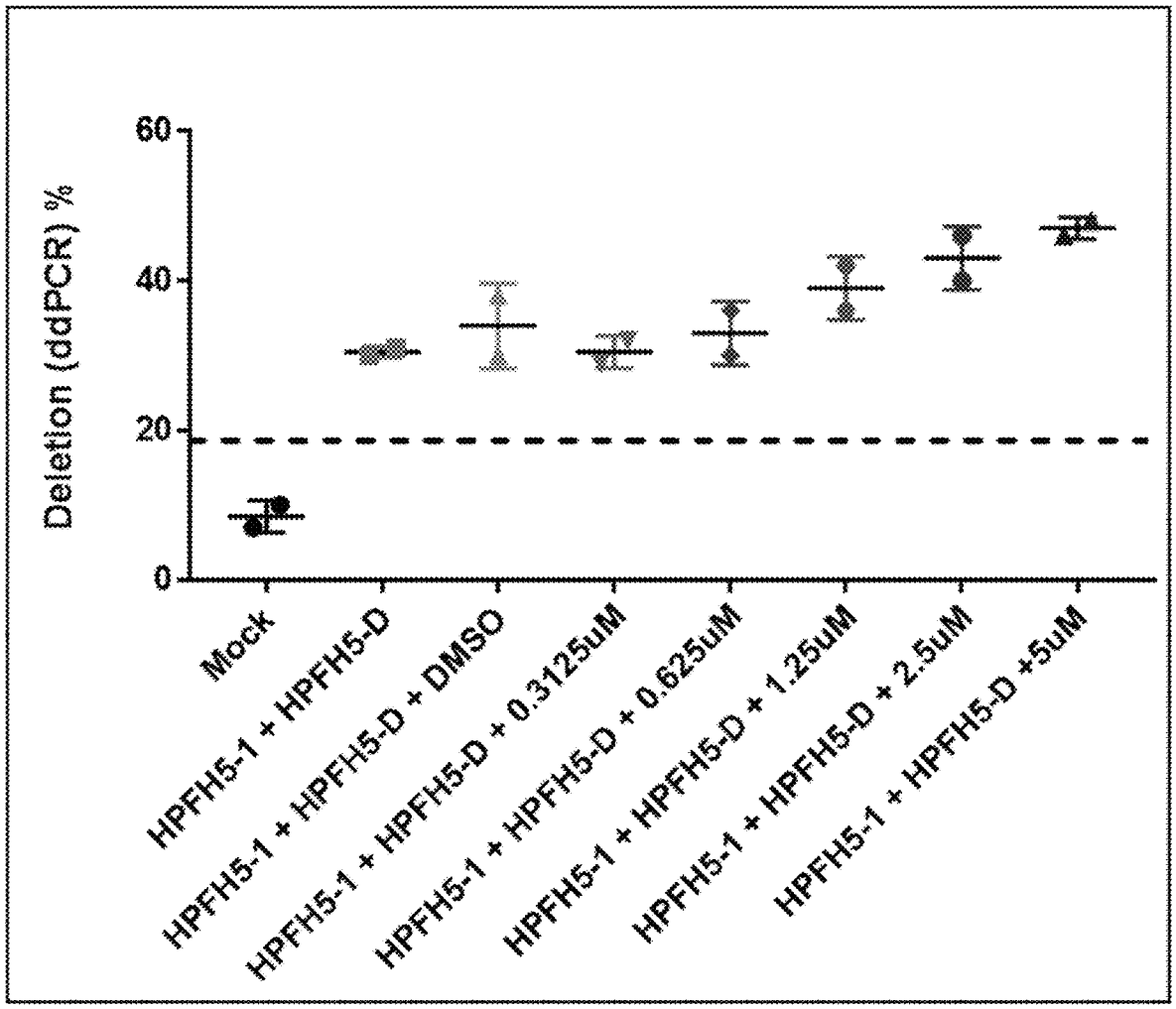
FIG. 4 is a graph showing the percentage of HPFH5 deletions in CD34+ hHSPCs edited with Cas9, the indicated gRNAs, and increasing doses of Nu7441 at 48 hours post electroporation. The data shows that NHEJ inhibition increases bulk HPFH5 deletion in a dose-dependent manner from 30% to 40%.

The deletion frequency was determined by droplet digital PCR (ddPCR) two days after electroporation for each of the cells electroporated with HPFH5-1+HPFH5-D gRNAs, or cells electroporated with HPFH5-5+HPFH5-D gRNAs. Results show that the addition of Nu7441 increased deletion efficiency from 30% to 45% in a dose-dependent manner (FIG. 4).

Figure 5A:
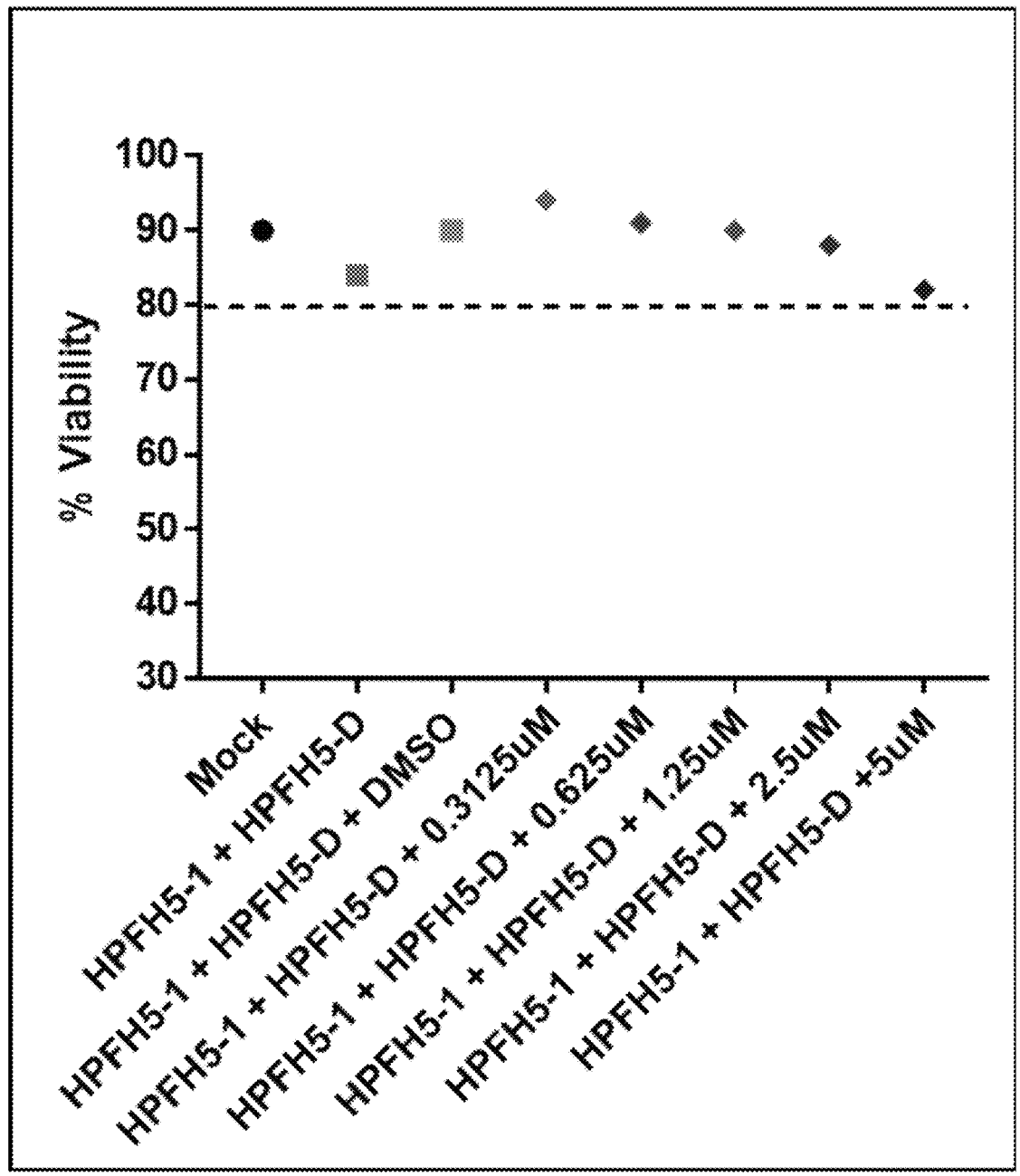
FIG. 5A is a graph showing percent viability in CD34+ hHSPCs edited with Cas9, the indicated gRNAs, and increasing doses of Nu7441 at 48 hours post electroporation. Nu7441 did not adversely affect cell viability concentrations of less than 5 μM.

Cell viability was also assessed using Trypan blue, a standard method for detecting hematopoietic stem cell viability. Cell viability was slightly reduced in cells that received the highest dose Nu7441 (5 µM) (FIG. 5A).

Figure 5B:
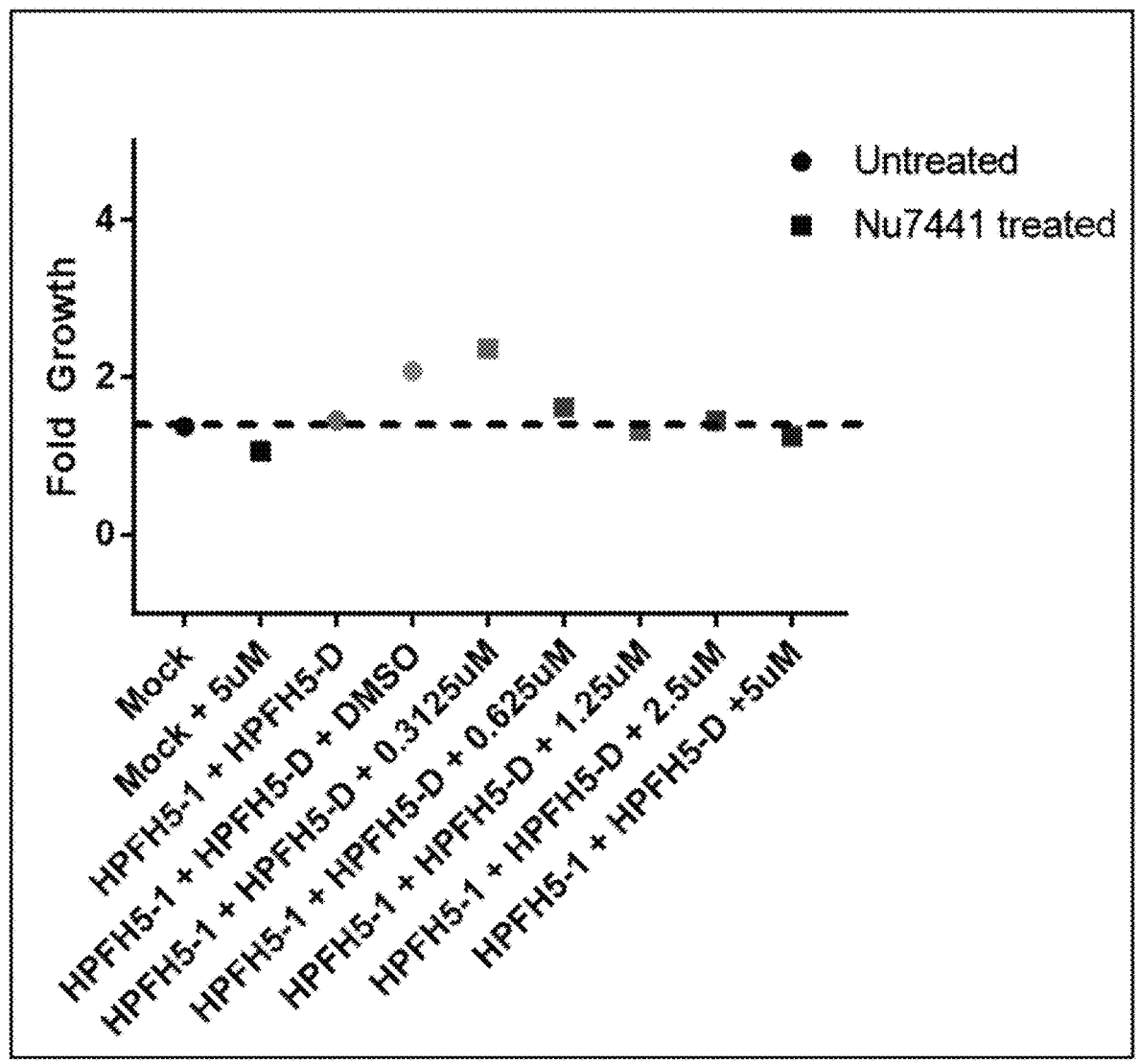
FIG. 5B is a graph showing fold growth in CD34+ hHSPCs edited with Cas9, the indicated gRNAs, and increasing doses of Nu7441 at 48 hours post electroporation. Nu7441 did not adversely affect cell proliferation at concentrations of less than 5 μM.

Cell proliferation was also assessed using a cell counting device (hemocytometer). Results show that cell proliferation was reduced at the highest concentration of Nu7441 (FIG. 5B).

Example 4. Effects of Nu7441 on Single gRNA Indel Frequency

Tracking of Indels by Decomposition (TIDE) was utilized to determine if treatment with Nu7441 results in increased single gRNA indels as a result of NHEJ inhibition. This technology precisely determines the spectrum and frequency of indels and MMEJ species generated by single HPFH5-1 gRNA or HPFH5-D gRNAs in the presence of Nu7441 by comparing the results of standard PCR reactions and Sanger sequencing reactions.

Figure 6:
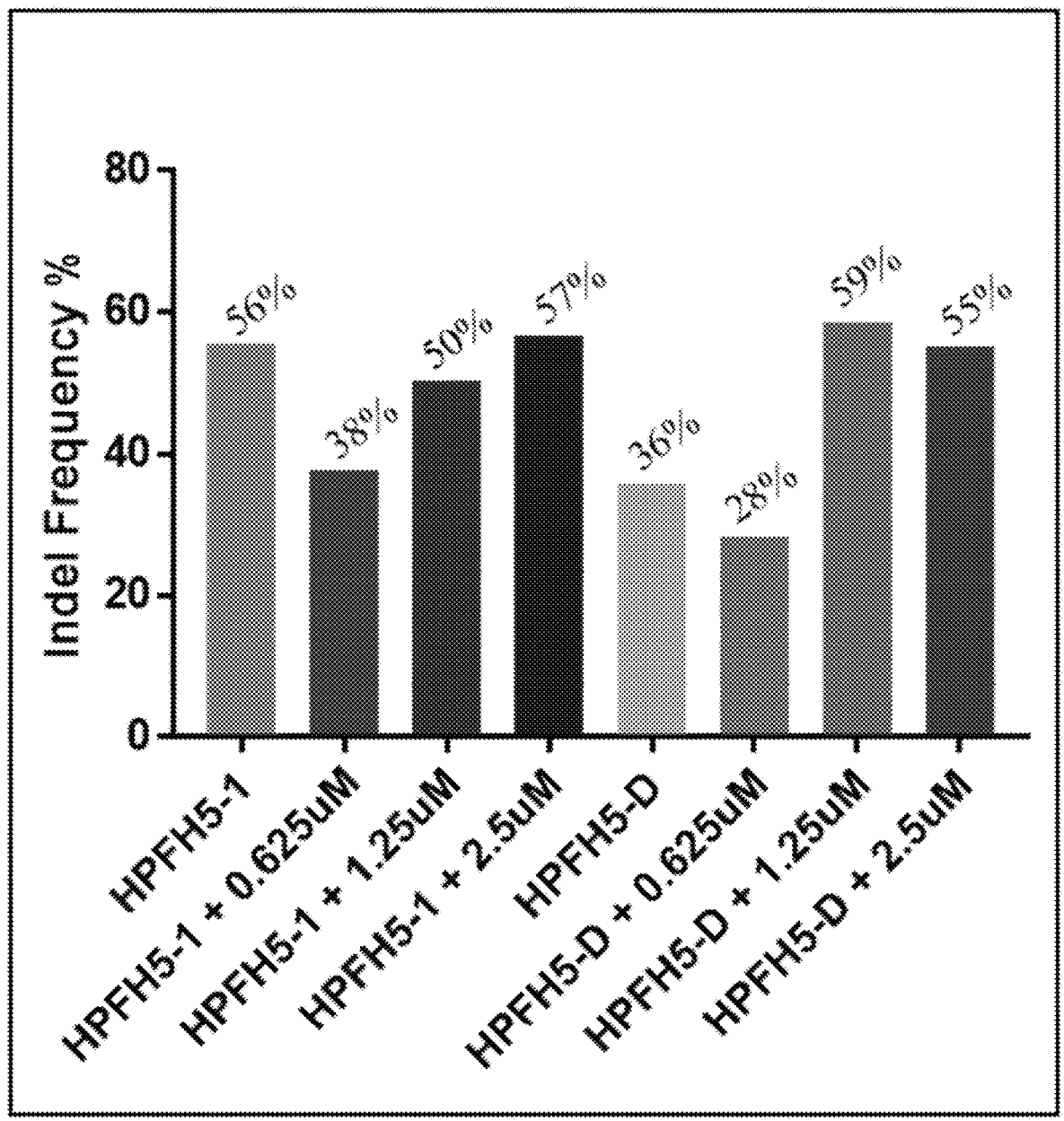
FIG. 6 is a graph showing percent indel (insertion/deletion) frequency in CD34+ hHSPCs edited with Cas9, the indicated single gRNAs, and increasing doses of Nu7441 at 48 hours post electroporation.

Cells were electroporated with 1.5 µg Cas and 1.5 µg HPFH5-D or 1.5 µg HPFH5-1 or no gRNA. Cells were treated with 0, 0.625 µM, 1.25 µM, 2.5 µM, or 5 µM Nu7441. Nu7441 had not major effects on single guide editing using HPFH5-1, whereas higher concentrations of Nu7441 increased indel frequency with HPFH5-D (FIG. 6).

Figure 7A:
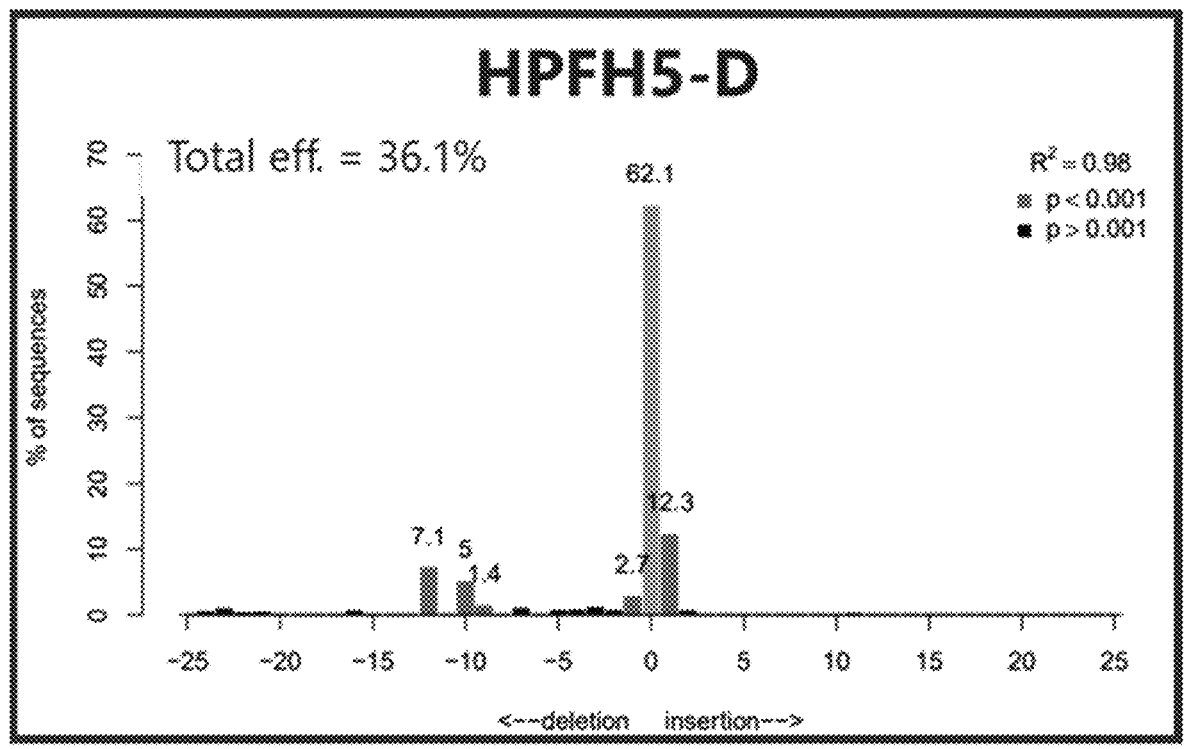
FIG. 7A is a graph showing microhomology-mediated end joining (MMEJ) species generated by Cas9 and HPFH5 gRNA.
Figure 7B:
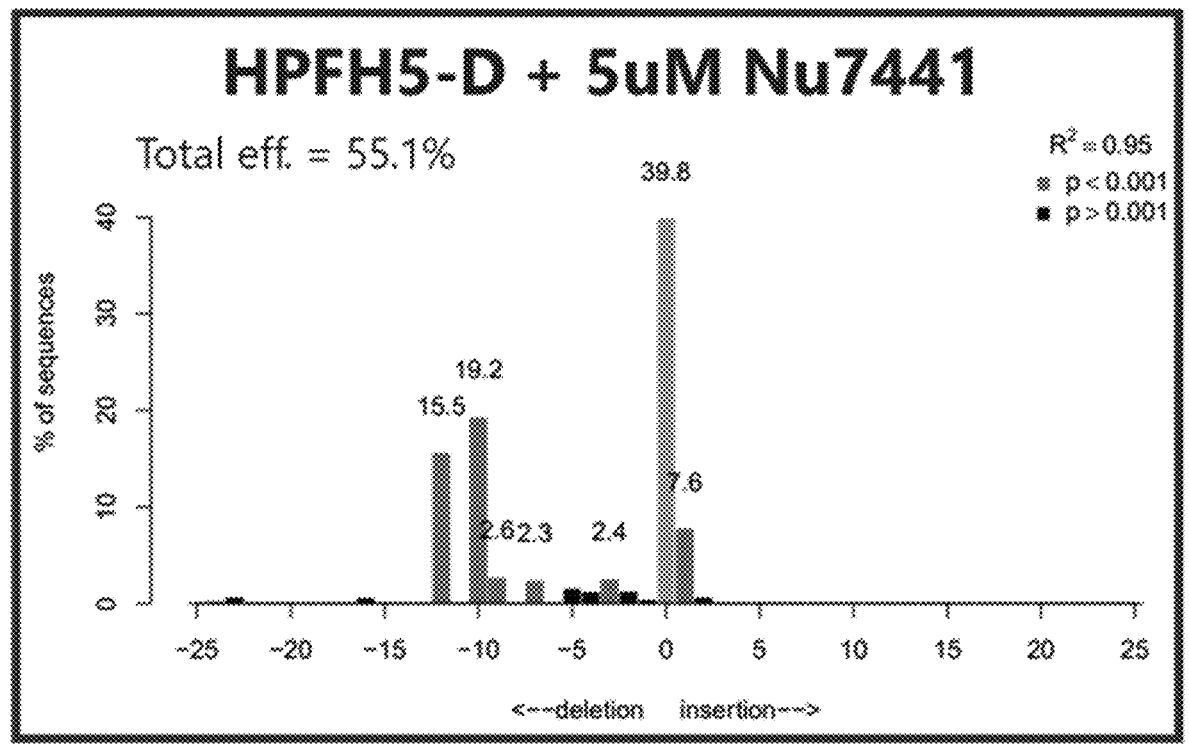
FIG. 7B is a graph showing the potential microhomology-mediated end joining (MMEJ) species generated by Cas9 and HPFH5 gRNA is increased in the presence of Nu7441.

The combination of the HPFH5-D gRNA and Nu 7441 (5 µM) resulted in an increase in the percentage of 10-15 base pair deletions and a decrease in the number of wild-type sequences in HPFH5 relative to untreated cells (FIG. 7).

Example 5. Effects of Nu7441 on HPFH5 Deletion—CFU Assays

The effects of Nu7441 on CRISPR-Cas9 gene editing using the dual gRNA approach (HPFH5-1 and HPFH5-D) was measured using a colony forming assay (CFU). CFU assay is an in vitro cellular assay that measures the proliferation and differentiation potential of human HSPCs. Following electoporation with dual gRNAs/Cas9 and treatment with Nu7441 (2.5 µM), CD34+ hHSPCs were diluted and plated in suspension in the presence of methylcellulose to promote stem cell differentiation. After 14 days, colonies grown from single erythroid-lineage HSPCs were analyzed for gene editing by ddPCR (Table 3).

TABLE 3

HPFH5-1 and HPFH5-D Clonal Editing

|  | HPFH5-1 + HPFH5-D | HPFH5-1 + HPFH5-D + 2.5 µM Nu7441 |
| --- | --- | --- |
| % Homozygotes | 15.4% | 17.3% |
| % Heterozygotes | 15.4% | 46.2% |
| % WT | 69.2% | 36.5% |
| Total clones | 52 | 52 |
| Total alleles | 104 | 104 |
| # Edited alleles | 24 | 42 |
| % Alleles edited from clones | 23% | 40% |
| Bulk editing from ddPCR | 30% | 43% |
| % Edited cells | 31% | 63% |

The percentage of HPFH5 heterozygotes was increased 3-fold in the presence of 2.5 µM Nu7441, relative to untreated cells. Additionally, the number of alleles edited from clones was increased 2-fold in the presence of Nu7441. These results indicate that NHEJ inhibition increases deletion in the presence of both gRNAs.

Example 6. Nu7741 Increased Frequency of Deletions in CCR5

Figure 8:
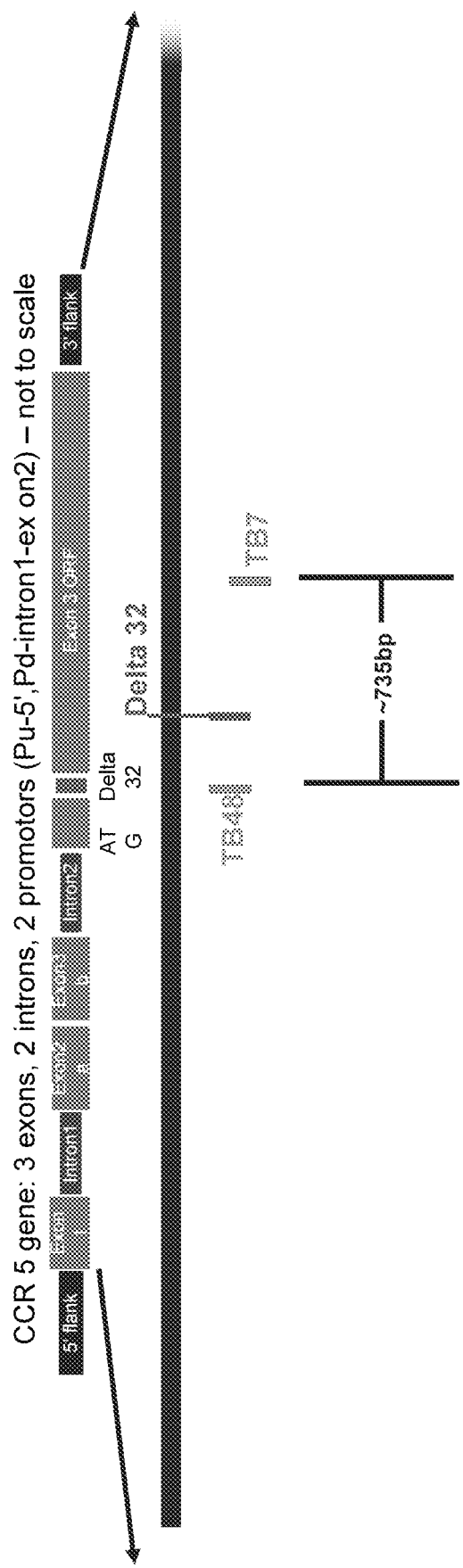
FIG. 8 is a schematic depicting the structure of the CCR5 gene and the locations of the TB48 gRNA and the TB7 gRNA target sites.

The C-C chemokine receptor type 5 (CCR5) is a key player in HIV infection due to its major involvement in the infection process. A limited number of people harbor a genomic 32-bp deletion in the CCR5 gene (CCR5432), leading to expression of a truncated gene product that provides resistance to HIV-1 infection in individuals homozygous for this mutation. Dual gRNAs were designed to target this region of the CCR5 gene. FIG. 8 diagrams the CCR5 gene and the location of TB48 gRNA and TB7 gRNA target sites (bordering a 735 bp deletion).

Figure 9:
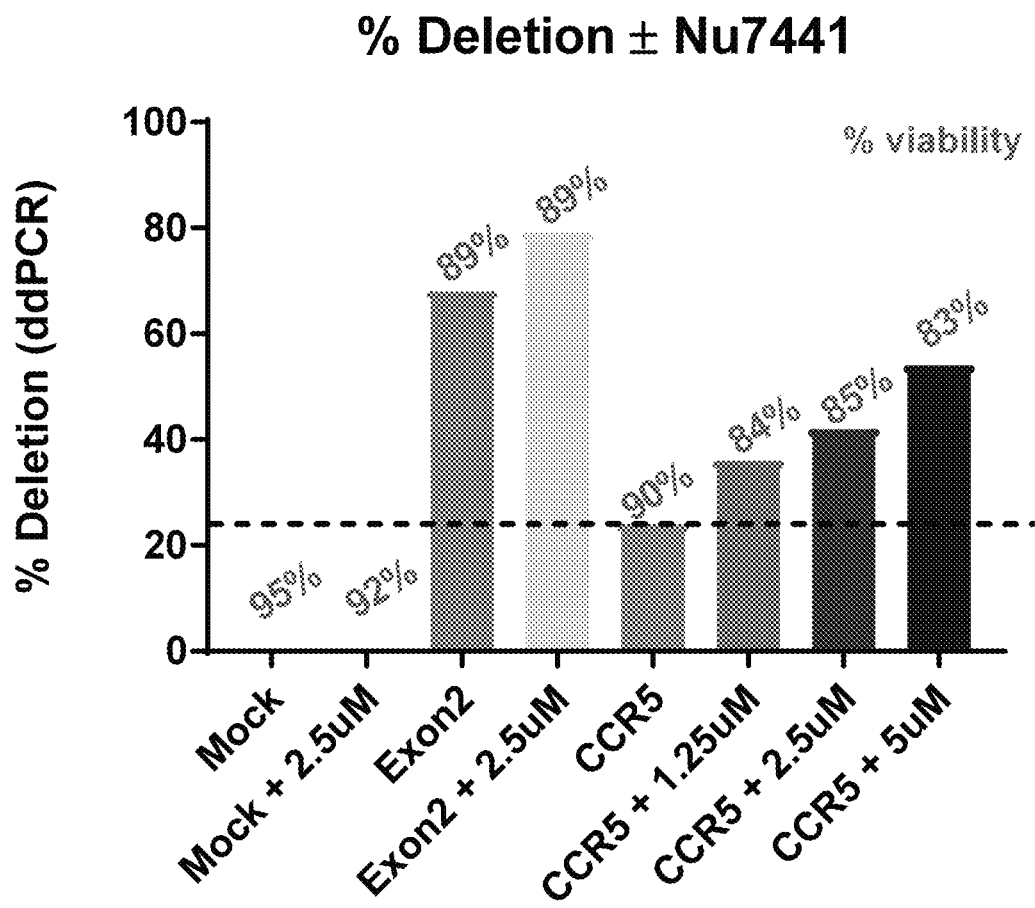
FIG. 9 is a graph showing the percentage CCR5 deletions in CD34+ hHSPCs edited with Cas9, the indicated gRNAs, and increasing doses of Nu7441 at 48 hours post electroporation. The percent viability is presented above each bar.

Human peripheral blood CD34+ cells were cultured and as electroporated with Cas9 and the two gRNAs essentially as described above in Example 1. Nu7441 was delivered to the cells (0, 1.25, 2.5, 5 µM) immediately after electroporation. Deletion efficiency was determined by ddPCR two days after electroporation. Nu774 increased the frequency of deletion in CCR5 in a dose-dependent manner (FIG. 9). The highest dose of Nu7441 increased the percent of deletions more than two-fold. Cell viability was decreased slightly at the highest concentration of Nu7441 (FIG. 9).

Figure 10:
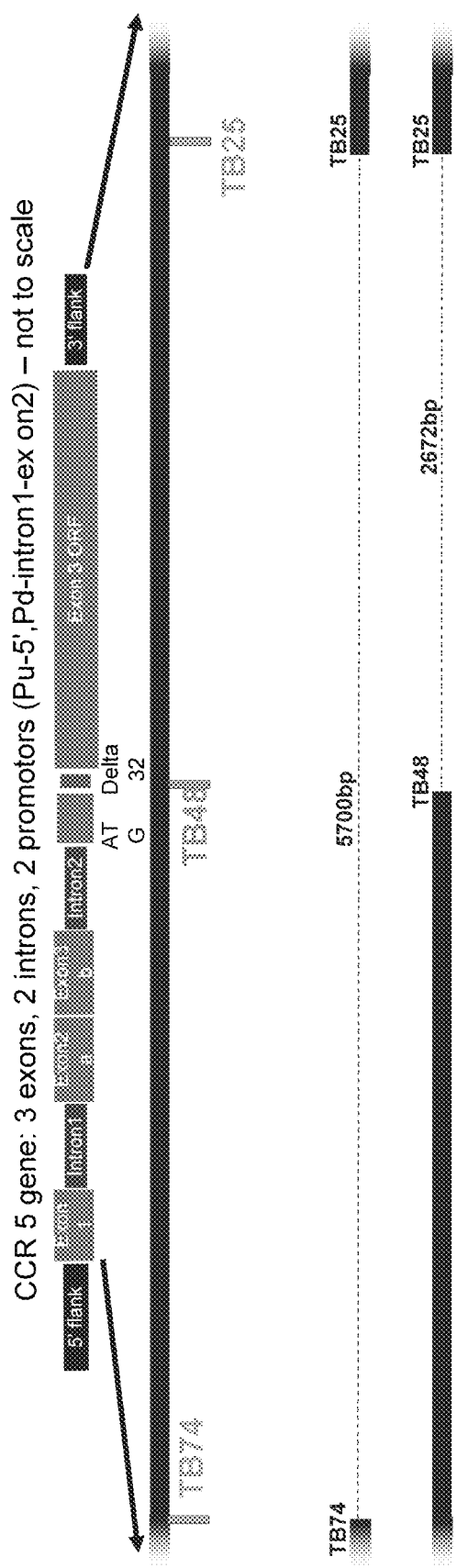
FIG. 10 is a schematic of the CCR5 gene with the location of additional gRNA sites; namely, the TB74 gRNA, TB 49 gRNA, and TB25 gRNA target sites. Two different sized deletions are depicted at the bottom.
Figure 11A:
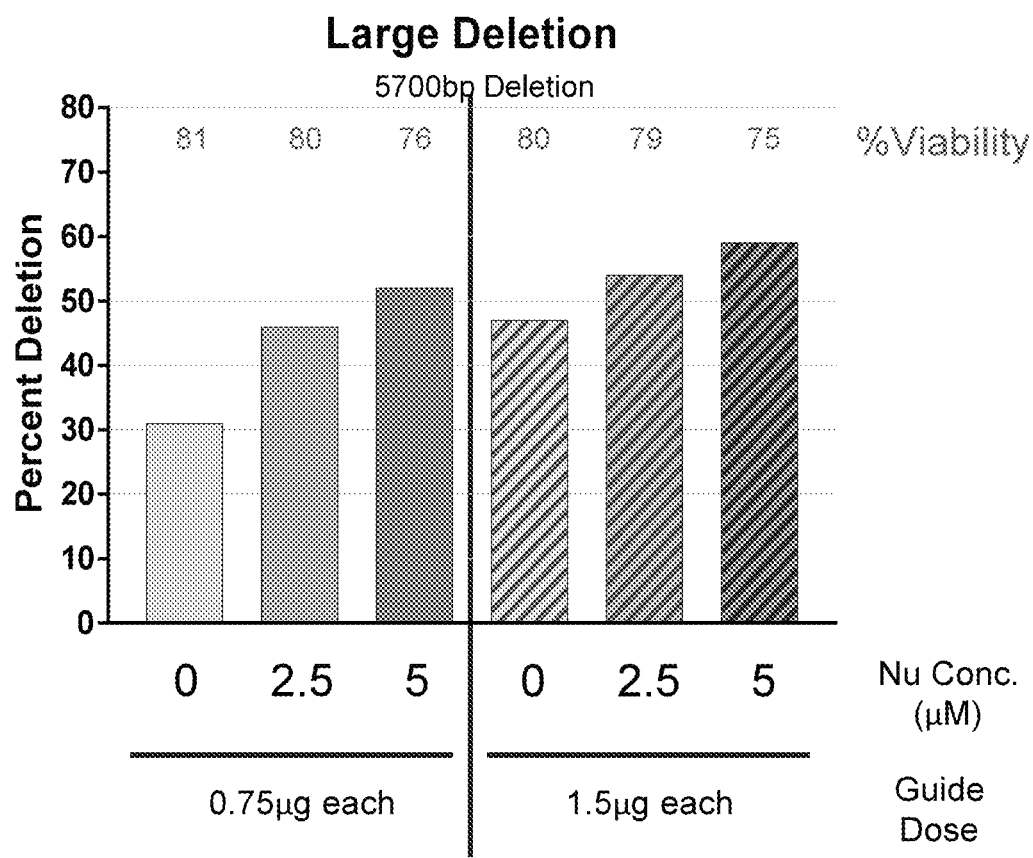
FIG. 11A is a graph showing the percentage of CCR5 deletions in CD34+ hHSPCs edited with Cas9, TB74 gRNA+TB25 gRNA (at the indicated doses), without or with the indicated doses of Nu7441 at 48 hours post electroporation. The percent viability is presented above each bar.
Figure 11B:
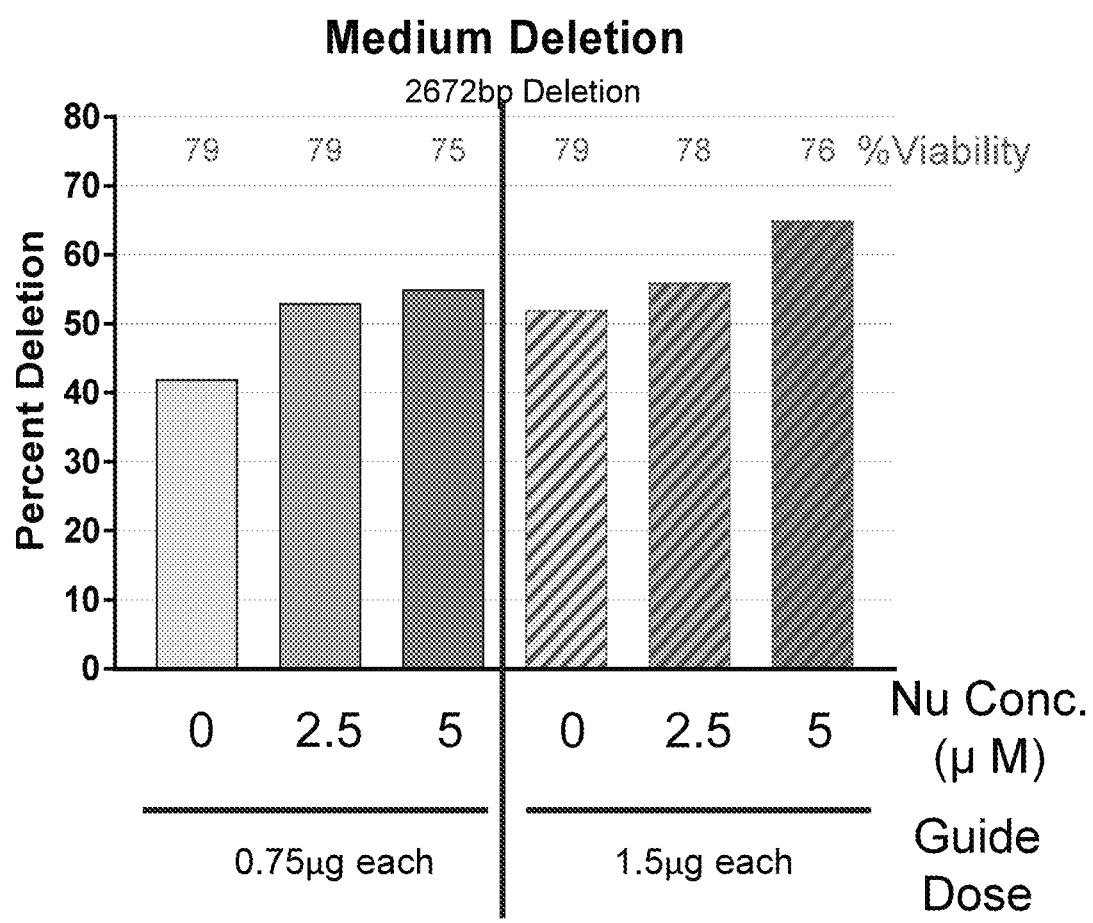
FIG. 11B is a graph showing the percentage of CCR5 deletions in CD34+ hHSPCs edited with Cas9, TB48 gRNA+TB25 gRNA (at the indicated doses), without or with the indicated doses of Nu7441 at 48 hours post electroporation. The percent viability is presented above each bar.

Additional gRNAs were designed to delete larger segments from CCR5, i.e., TB74 and TB 25 for a 5700 bp deletion, and TB48 and TB25 for a 2672 bp deletion (FIG. 10). The gRNAs (and Cas9) were introduced at two dose levels (0.75 or 1.5 µg each) and cells were exposed to 0, 2.5, or 5 µM Nu7441. As shown in FIG. 11, Nu7741 increased the percent of deletions by about 20-70% under all conditions.

Example 7. M3814 Increased Frequency of Deletions in CCR5

Figure 12A:
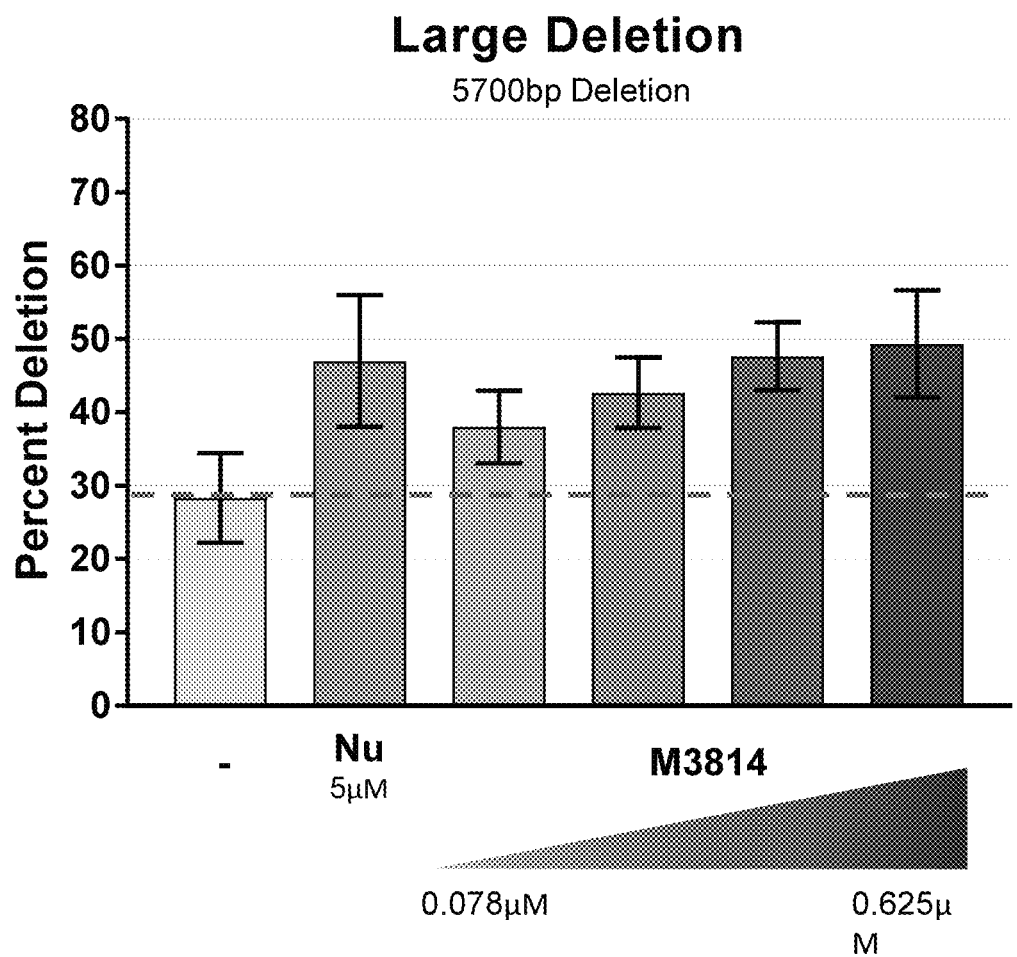
FIG. 12A is a graph showing the percentage of CCR5 deletions in CD34+ hHSPCs edited with Cas9 (37.5 μg/mL), TB74 gRNA+TB25 gRNA (75 (μg/mL of each), without or with the indicated doses of M3814 at 48 hours post electroporation.
Figure 12B:
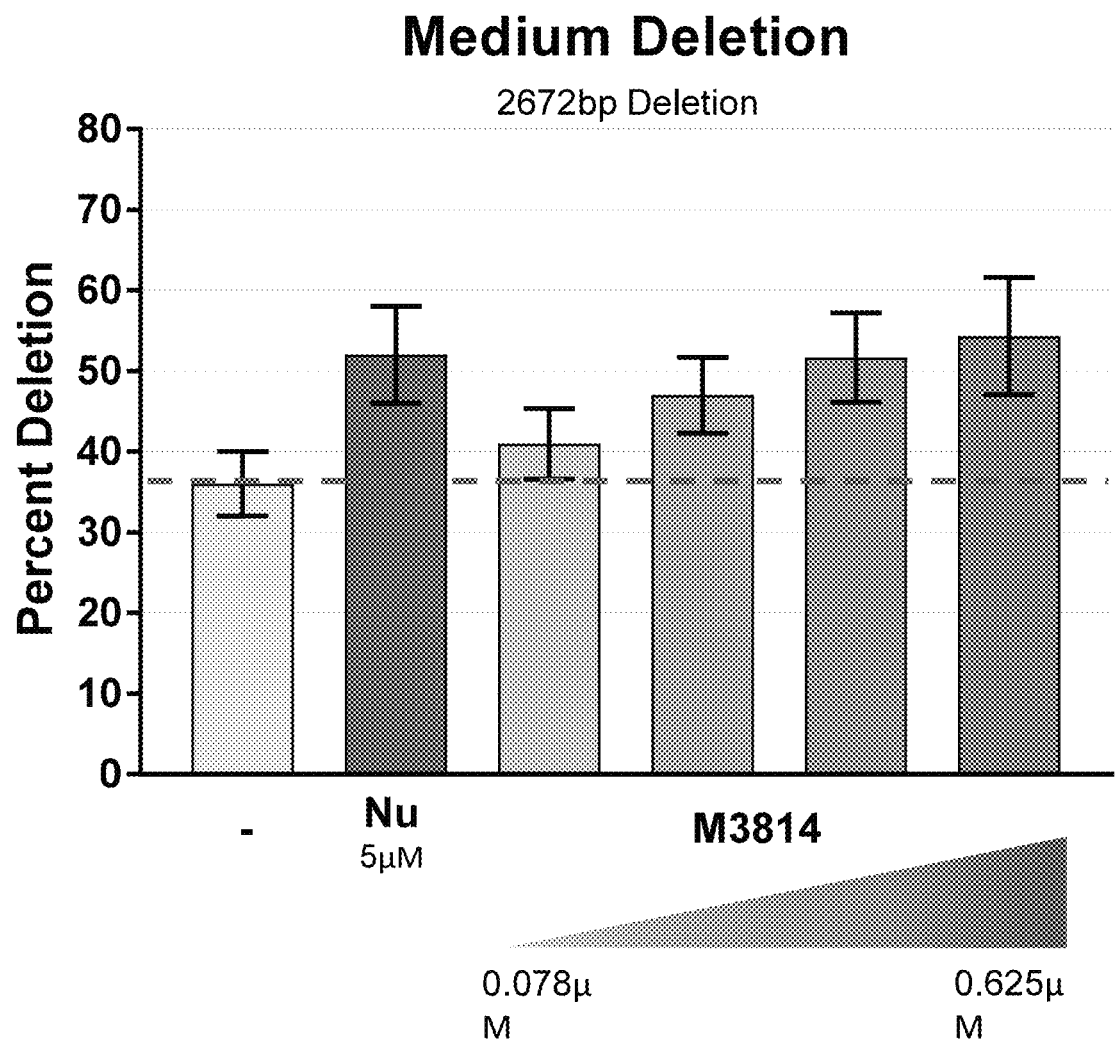
FIG. 12B is a graph showing the percentage of CCR5 deletions in CD34+ hHSPCs edited with Cas9 (37.5 μg/mL), TB48 gRNA+TB25 gRNA (75 (μg/mL of each), without or with the indicated doses of M3814 at 48 hours post electroporation.

Another DNA-PK inhibitor, M3814, was tested to determine whether deletions were increased in its presence. Populations of newly electroporated cells were exposed to four concentrations of M3814 ranging from 0.078 µM to 0.625 µM. The percentage of deletions was increased in a dose-dependent manner, with the highest concentration achieving about the same percentage increase in deletions as Nu7441 (FIG. 12).

What is claimed is:

1. A method for increasing efficiency of a targeted deletion of a chromosomal sequence, the method comprising:
   (a) delivering to a population of cells:
      (i) a CRISPR nuclease or a nucleic acid encoding a CRISPR nuclease, wherein the CRISPR nuclease is a Cas9 endonuclease;
      (ii) a first gRNA targeting a first site in chromosomal sequence and second gRNA targeting a second site in chromosomal sequence, or a nucleic acid encoding a first gRNA targeting a first site on the chromosomal sequence and a nucleic acid encoding a second gRNA targeting a second site on the chromosomal sequence, wherein the distance between the first site and the second site in the chromosomal sequence is about 1 kilobase pair to about 100 kilobase pairs; and
      (iii) a DNA-dependent protein kinase (DNA-PK) inhibitor; and
   (b) increasing the frequency of non-homologous end joining between the first site and the second site, thereby generating a targeted deletion between the first site and the second site in chromosomal sequence,
   wherein the targeted deletion in (b) occurs in the population of cells in an increased frequency that is at least 30% higher as compared to a population of control cells in which only (i) and (ii) are delivered.

2. The method of claim 1, wherein the CRISPR nuclease is a *Streptococcus pyogenes* Cas9 endonuclease or a *Staphylococcus aureus* Cas9 endonuclease.

3. The method of claim 1, wherein the CRISPR nuclease comprises one or more nuclear localization signals (NLSs).

4. The method of claim 1, wherein each of the first and second gRNAs is a single-molecule gRNA.

5. The method of claim 1, wherein each of the first and second gRNAs comprises one or more 2'-O-methyl phosphorothioate nucleotides.

6. The method of claim 1, wherein the DNA-PK inhibitor is chosen from Nu7441 (8-(4-Dibenzothienyl)-2-(4-morpholinyl)-4H-1-benzopyran-4-one); M3814 (S)-(2-chloro-4-fluoro-5-(7-morpholinoquinazolin-4-yl)phenyl)(6-methoxypyridazin-3-yl)methanol; NU 7026 (2-(4-morpholinyl)-4H-naphthol[1,2-b]pyran-4-one); compound 401 (2-(4-morpholinyl)-4H-pyrimido[2,1-a]isoquinolin-4-one), PI 103 hydrochloride (3-[4-(4-morpholinylpyrido[3',2':4,5]furo[3,2-d]pyrimidin-2-yl]phenol hydrochloride); DMNB (4,5-dimethoxy-2-nitrobenzaldehyde); ETP 45658 (3-[1-methyl-4-(4-morpholinyl)-1H-pyrazolo[3,4-d]pyrimidin-6-ylphenol), KU 0060648 (4-ethyl-N-[4-[2-(4-morpholinyl)-4-oxo-4H-1-benzopyran-8-yl]-1-dibenzothienyl]-1-piperazineacetamide); LTURM 34 (8-(4-dibenzothienyll)-2-(4-morpholinyl)-4H-1,3-benzoxazin-4-one); 1-(2-hydroxy-4-morpholin-4-yl-phenyl)-ethanone; PIK-75 HCl (2-methyl-5-nitro-2-[(6-bromoimidazo[1,2-a]pyridin-3-yl)methylene]-1-methylhydrazide-benzenesulfonic acid, monohydrochloride); or CC-115 (1-ethyl-7-(2-methyl-6-(1h-1,2,4-triazol-3-yl)pyridin-3-yl)-3,4-dihydropyrazino(2,3-b)pyrazin-2(1h)-one).

7. The method of claim 1, wherein the DNA-PK inhibitor is Nu7441 or M3814.

8. The method of claim 1, wherein the DNA-PK inhibitor is delivered at a concentration from about 0.05 μM to about 5 μM.

9. The method of claim 1, wherein (i) and (ii) are delivered to the population of cells prior to delivery of (iii).

10. The method of claim 1, wherein (i) and (ii) are delivered to the population of cells simultaneously with (iii).

11. The method of claim 1, wherein (i) and (ii) are delivered to the population of cells after delivery of (iii).

12. The method of claim 1, wherein the targeted deletion has a size from about 1 kb to about 3 kb, or from about 3 kb to about 10 kb.

13. The method of claim 1, wherein the targeted deletion has a size from about 10 kb to about 30 kb, or from about 30 kb to about 100 kb.

14. The method of claim 1, wherein the deletion is in hereditary persistence of fetal hemoglobin 5 (HPFH5) chromosomal region or in C-C chemokine receptor type 5 (CCR5) chromosomal region.

15. The method of claim 1, wherein the population of cells is chosen from hematopoietic stem and progenitor cells (HSPCs), hematopoietic stem cells (HSCs), mesenchymal stem cells (MSCs), induced pluripotent stem cells (human iPSCs), or immune cells.

16. The method of claim 1, wherein the population of cells is of human origin.

17. The method of claim 1, wherein the population of cells is an in vitro population of cells.

18. The method of claim 1, wherein the population of cells is an ex vivo population of cells extracted from a subject.

19. The method of claim 1, wherein the population of cells is an in vivo population of cells within a subject.

20. The method of claim 1, wherein the targeted deletion in (b) occurs in the population of cells in a frequency at least 40% higher as compared to a population of control cells in which only (i) and (ii) are delivered.

21. The method of claim 1, wherein the deletion frequency in the population of cells is at least 40%.

* * * * *